US007632495B2

(12) United States Patent
Levy

(10) Patent No.: US 7,632,495 B2
(45) Date of Patent: Dec. 15, 2009

(54) USE OF SOLUBLE FGL2 AS AN IMMUNOSUPPRESSANT

(75) Inventor: Gary Levy, Thornhill (CA)

(73) Assignee: Veritas Therapeutics Inc., Thornhill, Ontario (CA)

( * ) Notice: Subject to any disclaimer, the term of this patent is extended or adjusted under 35 U.S.C. 154(b) by 412 days.

(21) Appl. No.: 10/504,328

(22) PCT Filed: Feb. 28, 2003

(86) PCT No.: PCT/CA03/00273

§ 371 (c)(1), (2), (4) Date: Mar. 11, 2005

(87) PCT Pub. No.: WO03/074068

PCT Pub. Date: Sep. 12, 2003

(65) Prior Publication Data

US 2005/0164923 A1 Jul. 28, 2005

Related U.S. Application Data

(60) Provisional application No. 60/361,056, filed on Mar. 1, 2002.

(51) Int. Cl.
*A61K 39/395* (2006.01)
*A61K 39/00* (2006.01)
*C07K 16/00* (2006.01)

(52) U.S. Cl. .................. 424/130.1; 424/184.1; 530/300

(58) Field of Classification Search ....................... None
See application file for complete search history.

(56) References Cited

U.S. PATENT DOCUMENTS 5,254,339 A * 10/1993 Morein .................... 424/191.1
6,403,089 B1 * 6/2002 Levy et al. ............... 424/139.1
2006/0078550 A1 * 4/2006 Levy et al. ................. 424/94.2

FOREIGN PATENT DOCUMENTS

WO WO 98/51335 * 11/1998

OTHER PUBLICATIONS

Feldmann et al. Nature 2005, 435:612-619.*
Bach et al. Transplantation Immunology 1995, published by Wiley-Liss, Inc. Chapter 7, pp. 142-145.*
Kahan. Cur. Opin. Immunol., 1992; 4:553-560.*
Tufveson et al. Immunological Reviews, 1993; 136:99-109.*
Camie et al. The Journal of Immunology. 2003; 170:4036-4044.*
Liu et al. Eur. J. Immunol. 2008. 38:1-14. Copy is not provided.*
Sakaguchi et al. Nat. Immunol. 2005 Apr; 6(4):345-352.*
Chan, C.W.Y. et al., The Journal of Immunology, vol. 170. No. 8, pp. 4036-4044, Apr. 2003.
Ruegg, C et al., Gene, vol. 160, No. 2, pp. 257-262, Jul. 1995.
Chan, C.W.Y. et al., The Journal of Immunology, vol. 168. No. 10, pp. 5170-5177, May 2002.
Marazzi, S. et al, The Journal of Immunology, vol. 161, No. 1, pp. 138-147, Jul. 1998.
Koyama, T et al., Proceedings of the National Academy of Sciences, vol. 84, No. 84, pp. 1609-1613, Mar. 1987.
Yuwaraj, S et al., Genomics, vol. 71, No. 3, pp. 330-338, Feb. 2001.
Levy, G.A. et al., American Journal of Pathology, vol. 156, No. 4, pp. 1217-1225, Apr. 2000.

* cited by examiner

*Primary Examiner*—Maher M Haddad
*Assistant Examiner*—Chun Dahle
(74) *Attorney, Agent, or Firm*—Bereskin & Parr LLP; Melanie Szweras

(57) ABSTRACT

Methods and compositions for inducing immune suppression are disclosed. The methods involve administering an effective amount of a soluble fgl2 protein or a nucleic acid encoding a soluble fgl2 protein. The methods are useful in preventing graft rejection, autoimmune disease, and allergies.

6 Claims, 15 Drawing Sheets

(a)

65 kDa 1 2 3

(b)

65 kDa 1 2 3 a b

FIGURE 12A

Con A stimulated T cell truncated mfgl2 sequence

Truncation Fragment 1

Open Reading Frame atggaggaggtgctcaaagaagtgcggaccctcaaggaagcagtggacagtctgaagaaatcctgcca
ggactgtaagttgcaggctgacgaccatcgagatcccggcgggaatggagggaatggagcagagacag
ccgaggacagtagagtccaggaactggagagtcaggtgaacaagctgtcctcagagctgaagaatgca
aaggaccagatccaggggctgcaggggcgcctggagacgctccatctggtaaatatgaacaacattgag
aactacgtggacaacaaagtggcaaatctaaccgttgtggtcaacagtttggatggcaagtgttccaagtgt
cccagccaagaacacatgcagtcacagccggttcaacatctaatatacaaagattgttccgaccactacgt
gctaggaaggagaagcagtggggcctacagagttacccctgatcacagaaacagcagctttgaggtcta
ctgtgacatggagaccatgggtggaggctggacggtgctgcaggctcgccttgatggcagcaccaacttca
ccagagagtggaaagactacaaagccggctttggaaaccttgaacgagaattttggttgggcaacgataa
aattcatcttctgaccaagagtaaggaaatgatttgagaatagatcttgaagactttaatggtctcacactttat
gccttgtatgatcagttttatgtggctaatgaatttctcaaataccgattacacatcggtaactacaatggcacg
ggaggggatgccttgcgtttcagtcgacactacaaccatgacctgaggtttttcacaaccccagacagaga
caacgatcggtacccctctgggaactgtgggctctattacagctcaggctggtggtttgattcatgtctctctgc
caacttaaatggcaaatattaccaccagaaatacaaaggtgtccgtaatgggattttctggggcacctggcc
tggtataaaccaggcacagccaggtggctacaagtcctccttcaaacaggccaagatgatgattaggccc
aagaatttcaagccataa

FIGURE 12B

Amino Acid Sequence

MEEVLKEVRTLKEAVDSLKKSCQDCKLQADDHRDPGGNGGNGAETAEDSR
VQELESQVNKLSSELKNAKDQIQGLQGRLETLHLVNMNNIENYVDNKVANLT
VVVNSLDGKCSKCPSQEHMQSQPVQHLIYKDCSDHYVLGRRSSGAYRVTP
DHRNSSFEVYCDMETMGGGWTVLQARLDGSTNFTREWKDYKAGFGNLER
EFWLGNDKIHLLTKSKEMILRIDLEDFNGLTLYALYDQFYVANEFLKYRLHIGN
YNGTGGDALRFSRHYNHDLRFFTTPDRDNDRYPSGNCGLYYSSGWWFDS
CLSANLNGKYYHQKYKGVRNGIFWGTWPGINQAQPGGYKSSFKQAKMMIR
PKNFKP

FIGURE 13A

Con A stimulated T cell truncated mfgl2 sequence

Truncation Fragment 2

Open Reading Frame atgaacaacattgagaactacgtggacaacaaagtggcaaatctaaccgttgtggtcaacagtttggatgg
caagtgttccaagtgtcccagccaagaacacatgcagtcacagccggttcaacatctaatatacaaagatt
gttccgaccactacgtgctaggaaggagaagcagtggggcctacagagttacccctgatcacagaaaca
gcagctttgaggtctactgtgacatggagaccatgggtggaggctggacggtgctgcaggctcgccttgatg
gcagcaccaacttcaccagagagtggaaagactacaaagccggctttggaaaccttgaacgagaattttg
gttgggcaacgataaaattcatcttctgaccaagagtaaggaaatgattttgagaatagatcttgaagacttta
atggtctcacactttatgccttgtatgatcagttttatgtggctaatgaatttctcaaataccgattacacatcggta
actacaatggcacgggaggggatgccttgcgtttcagtcgacactacaaccatgacctgaggtttttcacaa
ccccagacagagacaacgatcggtacccctctgggaactgtgggctctattacagctcaggctggtggtttg
attcatgtctctctgccaacttaaatggcaaatattaccaccagaaatacaaaggtgtccgtaatgggattttct
ggggcacctggcctggtataaaccaggcacagccaggtggctacaagtcctccttcaaacaggccaaga
tgatgattaggcccaagaatttcaagccataa

FIGURE 13B

Amino Acid Sequence

MNNIENYVDNKVANLTVVVNSLDGKCSKCPSQEHMQSQPVQHLIYKDCSDH
YVLGRRSSGAYRVTPDHRNSSFEVYCDMETMGGGWTVLQARLDGSTNFT
REWKDYKAGFGNLEREFWLGNDKIHLLTKSKEMILRIDLEDFNGLTLYALYD
QFYVANEFLKYRLHIGNYNGTGGDALRFSRHYNHDLRFFTTPDRDNDRYPS
GNCGLYYSSGWWFDSCLSANLNGKYYHQKYKGVRNGIFWGTWPGINQAQ
PGGYKSSFKQAKMMIRPKNFKP

FIGURE 14A

Con A stimulated T cell truncated mfgl2 sequence

Truncation Fragment 3

Open Reading Frame atgcagtcacagccggttcaacatctaatatacaaagattgttccgaccactacgtgctaggaaggagaag
cagtggggcctacagagttacccctgatcacagaaacagcagctttgaggtctactgtgacatggagacca
tgggtggaggctggacggtgctgcaggctcgccttgatggcagcaccaacttcaccagagagtggaaag
actacaaagccggctttggaaaccttgaacgagaattttggttgggcaacgataaaattcatcttctgaccaa
gagtaaggaaatgattttgagaatagatcttgaagactttaatggtctcacactttatgccttgtatgatcagtttt
atgtggctaatgaatttctcaaataccgattacacatcggtaactacaatggcacgggaggggatgccttgc
gtttcagtcgacactacaaccatgacctgaggtttttcacaaccccagacagagacaacgatcggtacccct
ctgggaactgtgggctctattacagctcaggctggtggtttgattcatgtctctctgccaacttaaatggcaaat
attaccaccagaaatacaaaggtgtccgtaatgggattttctggggcacctggcctggtataaaccaggca
cagccaggtggctacaagtcctccttcaaacaggccaagatgatgattaggcccaagaatttcaagccata
a

FIGURE 14B

Amino Acid Sequence

MQSQPVQHLIYKDCSDHYVLGRRSSGAYRVTPDHRNSSFEVYCDMETMGG
GWTVLQARLDGSTNFTREWKDYKAGFGNLEREFWLGNDKIHLLTKSKEMIL
RIDLEDFNGLTLYALYDQFYVANEFLKYRLHIGNYNGTGGDALRFSRHYNHD
LRFFTTPDRDNDRYPSGNCGLYYSSGWWFDSCLSANLNGKYYHQKYKGV
RNGIFWGTWPGINQAQPGGYKSSFKQAKMMIRPKNFKP

USE OF SOLUBLE FGL2 AS AN IMMUNOSUPPRESSANT

FIELD OF THE INVENTION

The present invention relates to methods and compositions for modulating an immune response. Specifically, the invention includes the use of the soluble fgl2 protein to suppress an immune response.

BACKGROUND OF THE INVENTION

Proteins homologous to the carboxyl terminus of the β and γ chains (fibrinogen-related domain or FRED[2]) of fibrinogen, including angiopoietins, ficolins and tenascins, have been classified into the fibrinogen-related protein superfamily and have been demonstrated to exert multifaceted roles in immune responses (1-3). For example, fibrinogen can act as a "bridge" between $\alpha_m\beta 2$-bearing leukocytes to ICAM-1 on endothelial cells, and the engagement of $\alpha_m\beta 2$ by fibrinogen triggers a series of intracellular signaling events and cellular responses including cytokine secretion and nuclear factor-κB activation (4, 5). Angiopoietin-1 inhibits endothelial cell permeability in response to thrombin and vascular endothelial growth factor in vitro via the regulation of the junctional complexes, PECAM-1 and vascular endothelial cadherin (6). Two independent studies have reported that soluble tenascin blocks T cell activation induced by soluble antigens, alloantigens, or the mitogen Con A (7, 8).

Fgl2, also known as fibroleukin, has been demonstrated to be involved in the pathogenesis of diseases including viral-induced fulminant hepatitis and Th1 cytokine-induced fetal loss syndrome, in which fibrin deposition is a prominent feature (9-11). The gene fgl2 was originally cloned from CTL and the encoded protein shares a 36% homology to the fibrinogen β and γ chains and a 40% homology to the FRED of tenascin (1, 12). The coagulation activity of fgl2 was first described in a murine fulminant hepatitis model (13, 14) and fgl2 prothrombinase was detected in activated reticuloendothelial cells (macrophages and endothelial cells) (9, 15, 16). Fgl2 functions as an immune coagulant with the ability to generate thrombin directly, and thus, fgl2 appears to play an important role in innate immunity.

Human fgl2/fibroleukin expressed by peripheral blood $CD4^+$ and $CD8^+$ T-cells has been shown to be a secreted protein devoid of coagulation activity (17, 18). However, the function for soluble fgl2 protein generated by T-cells has herebefore remained undefined.

SUMMARY OF THE INVENTION

The present inventor has demonstrated that soluble fgl2 protein inhibits T-cell proliferation induced by alloantigen, anti-CD3/anti-CD28 mAbs and Concanavalin-A (ConA) in a dose- and time-dependent manner. Promotion of a Th2 cytokine profile was observed in a fgl2-treated allogeneic response. In addition, fgl2 protein abrogated LPS-induced maturation of bone marrow-derived dendritic cells (DC), resulting in a reduced ability to induce alloreactive T cell proliferation. Further, in a rat to mouse skingraft xenotransplantation model, soluble fgl2 protein exhibits immunosuppressive properties as shown by the inhibition of T cells proliferation in a one way xeno-mixed lymphocyte reaction. All of these results indicate that soluble fgl2 is an effective immune suppressant and soluble fgl2 has properties distinct from the prothrombinase activity of membrane bound fgl2.

Consequently, the present invention provides a method of suppressing an immune response comprising administering an effective amount of a soluble fgl2 protein or a nucleic acid sequence encoding a soluble fgl2 protein to an animal in need of such treatment. The invention also includes a use of an effective amount of a soluble fgl2 protein or a nucleic acid sequence encoding a soluble fgl2 protein to suppress an immune response or in the manufacture of a medicament to suppress an immune response.

In one embodiment, the present invention provides a method of preventing or inhibiting T-cell proliferation and/or DC maturation comprising administering an effective amount of a soluble fgl2 protein or a nucleic acid sequence encoding a soluble fgl2 protein to an animal in need of such treatment. The invention includes a use of an effective amount of a soluble fgl2 protein or a nucleic acid sequence encoding a soluble fgl2 protein to prevent or inhibit T-cell proliferation and/or DC maturation or in the manufacture of a medicament to prevent or inhibit T cell proliferation and/or DC maturation.

In a further embodiment, the present invention provides a method of promoting a Th2 cytokine response comprising administering an effective amount of a soluble fgl2 protein or a nucleic acid sequence encoding a soluble fgl2 protein to an animal in need thereof. The invention includes a use of an effective amount of a soluble fgl2 protein or a nucleic acid sequence encoding a soluble fgl2 protein to promote a Th2 cytokine response or in the manufacture of a medicament to promote a Th2 cytokine response.

The present invention further provides a method of treating a disease or condition wherein it is desirable to suppress an immune response comprising administering an effective amount of a soluble fgl2 protein or a nucleic acid sequence encoding a soluble fgl2 protein to an animal in need of such treatment. The invention also includes a use of an effective amount of a soluble fgl2 protein or a nucleic acid sequence encoding a soluble fgl2 protein to treat a disease or condition wherein it is desirable to suppress an immune response or in the manufacture of a medicament to suppress an immune response.

The method of the invention may be used to treat any disease or condition wherein it is desirable to suppress an immune response, for example, to induce tolerance to transplanted organs or tissues, treating graft versus host disease, treating autoimmune diseases and treating allergies.

The invention also includes pharmaceutical compositions containing soluble fgl2 proteins or nucleic acids encoding soluble fgl2 proteins for use in suppressing an immune response.

The present invention also provides an antibody, preferably a monoclonal antibody, to soluble fgl2. In one embodiment, said monoclonal antibody binds proximate to the cleavage site of soluble fgl2 (e.g. the cleavage site of membrane/soluble fgl2).

The invention further provides a method for diagnosing a condition related to soluble fgl2 expression or activity. In one embodiment, said method comprises obtaining a biological sample from a patient (such as a blood or tissue sample) and incubating said sample with an antibody for soluble fgl2, preferably a monoclonal antibody, under conditions that permit formation of a soluble fgl2/antibody complex. Said method permits the detection and/or determination of the presence and or level of soluble fgl2 in the sample, the presence or particular level of soluble fgl2 being indicative of a soluble fgl2 related condition. In another embodiment, said antibody is a labelled antibody. In another embodiment, the amount of soluble fgl2 is determined by the amount of complexed soluble fgl2 with said soluble fgl2, either directly or indirectly. For instance, if a particular amount of antibody is used, then the amount of complexed or remaining uncomplexed (or free) antibody can be measured to infer the amount of soluble fgl2 present in the sample.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

LPS treated BM-derived DC. After 1 h of exposure to LPS or soluble fgl2+LPS immunostaining was carried out as described in the material and methods. Each Panel (a-f) shows the same cells visualized by immunofluorescence using different filters. Cells in (a) and (d) show red fluorescence anti-p65 staining. Cells in (b) and (e) show blue chromosomal DAPI staining. Panels (c) and (f) show an overlay of the anti-p65 and DAPI staining. The purple color represents cells that have p65 translocation. LPS exposed cells had marked NF-κB translocation shown by the accumulation of p65 in the nucleus, confirmed by DAPI nuclear staining (c). Incubation with soluble fgl2 during LPS exposure was able to inhibit NF-κB translocation shown by diffuse p65 staining and distinct blue of the DAPI staining in most of cells (f). B, Histogram showing the percent p65 NF-κB translocation in at T=1 h after LPS stimulation in soluble fgl2 treated and untreated groups. An average of 100 cells were counted from greater than 3 different fields. There is a significant reduction in p65 NF-κB translocation with soluble fgl2 treatment ($p<0.01$).

Figure 9:
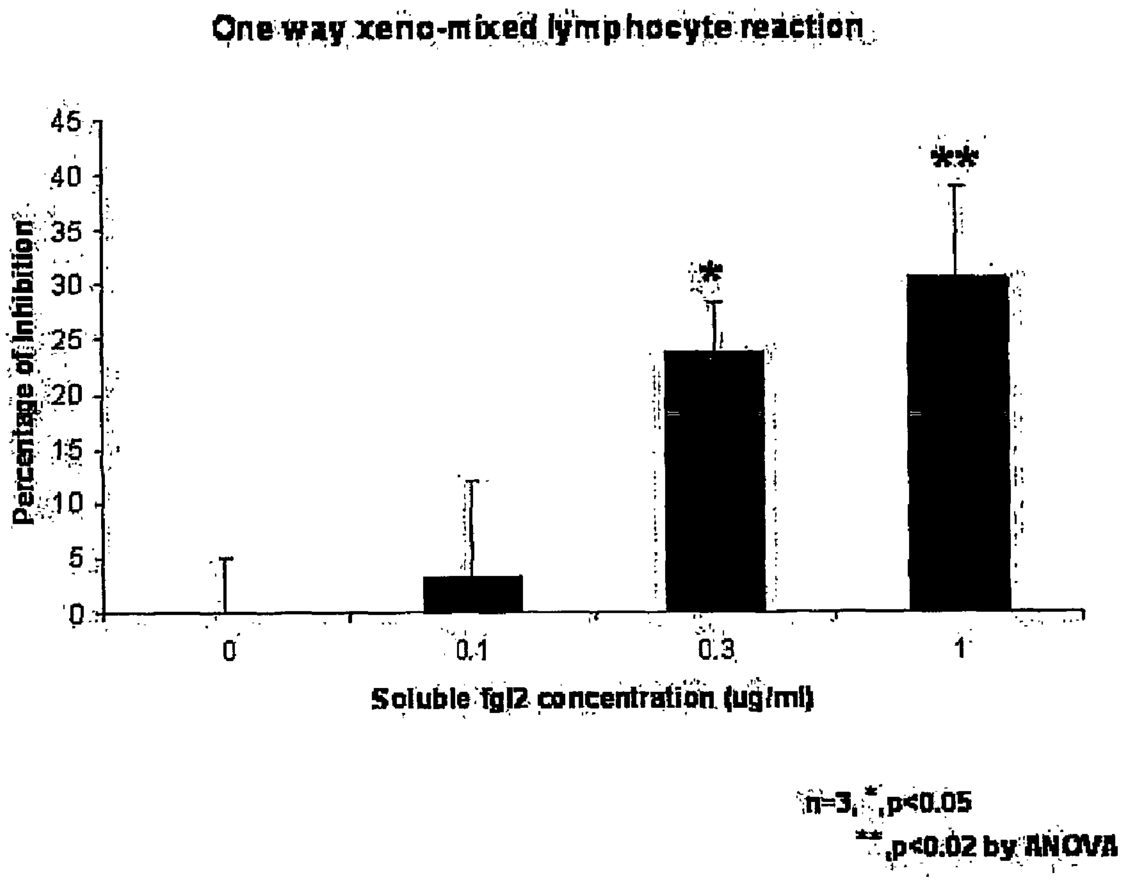

FIG. 9 is a graph showing the effects of fgl2 protein on T cell proliferation in a one-way xenogeneic mixed lymphocyte reaction. Fgl2 protein inhibited the proliferation of primed T cells re-challenged with the splenic cells of the Wistar rat origin in a dose-dependent manner. Proliferation was determined by [$^3$H] thymidine uptake in triplicate wells. The data are expressed as percentage of inhibition (fgl2-untreated samples are shown as 0% of inhibition) and are representative of three separate experiments. Statistical analysis was performed using the Student-Newman-Keuls method or one-way ANOVA. *, $p<0.05$ and **, $p<0.02$ compared with control groups (no fgl2 added).

Figure 10:
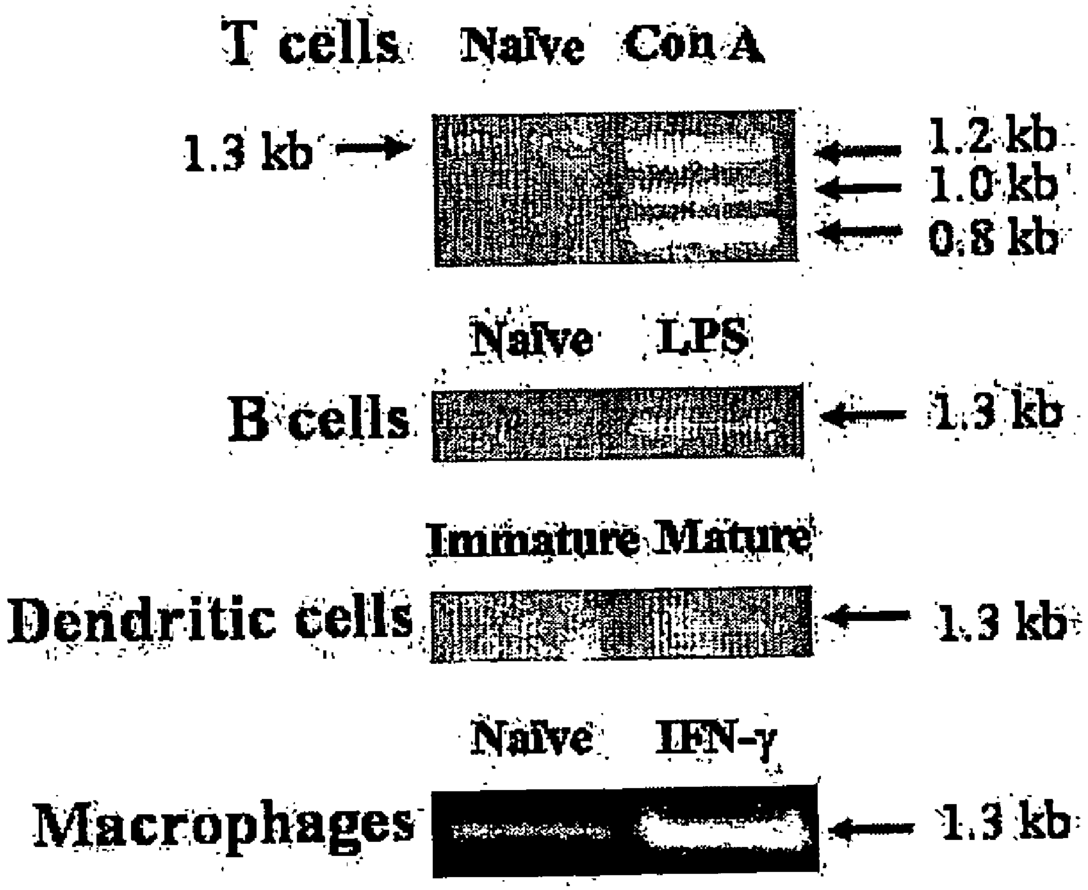

FIG. 10 shows 5'RACE analysis of fgl2 gene expression. Full length mRNA fgl2 transcripts were detected in naïve T cells (A), B cells stimulated with 10 mg/ml LPS for 3 days (B), immature and mature dendritic cells (C), naïve macrophages, and macrophages stimulated with 100 U/ml IFN-γ for 24 hrs (D), whereas fgl2 was not detected in naïve B cells (B). Three shorter fgl2 mRNA transcripts, corresponding to molecular sizes 1.2 kb, 1.0 kb and 0.8 kb were detected in T cells stimulated with 5 μg/ml Con A for 3 days (A).

Figure 11:
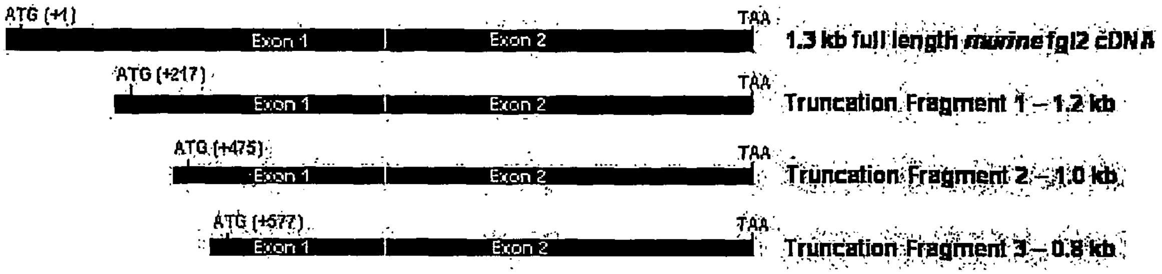

FIG. 11 shows the sequence analysis of the 5'RACE products. The sequences of the 1.3 kb band observed in the 5'RACE product of the antigen presenting cells and naïve T cells corresponded to the full length fgl2 mRNA and the resulting protein with the prothrombinase activity. The nucleotide position of the ATG translation start codon of the full length fgl2 mRNA is referred to as +1. The sequences of three short fgl2 mRNA transcripts seen in Con-A stimulated T cells indicated they were the result of alternative transcriptional start sites and not alternative splicing at the exon-intron junction. The longest open reading frames of the 1.2 kb, 1.0 kb and 0.8 kb fragments as determined by the first methionine codon with a Kozak consensus sequence would begin translation at the ATG nucleotide position +217, +475, and +577, respectively.

FIGS. 12A and B shows the nucleic acid sequence (FIG. 12A and SEQ ID NO:1) encoding truncation fragment 1 and the amino acid sequence of truncation fragment 1 (FIG. 12B and SEQ ID NO:2).

FIGS. 13A and B shows the nucleic acid sequence (FIG. 13A and SEQ ID NO:3) encoding truncation fragment 2 and the amino acid sequence of truncation fragment 2 (FIG. 13B and SEQ ID NO:4).

FIGS. 14A and B shows the nucleic acid sequence (FIG. 14A and SEQ ID NO:5) encoding truncation fragment 3 and the amino acid sequence of truncation fragment 3 (FIG. 14B and SEQ ID NO:6).

DETAILED DESCRIPTION OF THE INVENTION

The present inventor has provided the first evidence that soluble fgl2 protein exhibits immunomodulatory properties with suppressive effects on T-cell proliferation and DC maturation. Promotion of a Th2 cytokine response has been shown to improve transplant survival. The inventor has shown that addition of soluble fgl2 protein in a mixed leukocyte reaction resulted in an increased production of IL-4 and IL-10 and a decreased production of IL-2 and IFN-γ. The inventor has also shown that soluble fgl2 inhibits T cell proliferation in a one way xeno-mixed lymphocyte reaction in a rat to mouse skin graft xenotransplantation model.

DCs are professional antigen presenting cells (APCs) which exhibit a unique ability to stimulate both naïve and memory T-lymphocytes. Their potential to determine the balance between immunity and tolerance allows DCs to be a target for therapeutic manipulation of immune responses against alloantigens. It has been reported that bone marrow-derived immature DCs can induce hyper-responsiveness in allogeneic T-cells and significantly prolong cardiac allograft survival when injected into recipient mice (25). Herein it is demonstrated that soluble fgl2 prevented full maturation of DCs by lowering the expression levels of CD80$^{hi}$, CD86$^{hi}$ and MHC class II$^{hi}$. No significant effects on MHC class I, CD11c and CD40 expression were observed.

The present inventor has demonstrated that soluble fgl2 protein exhibits immunomodulatory properties with no direct prothrombinase activity. The findings that soluble fgl2 inhibited T-cell proliferation, promoted Th2 cytokine expression and prevented DC maturation suggest a novel usage of soluble fgl2 protein as an immunosuppressive agent which may induce T-cell tolerance and therefore improve graft survival.

I. Soluble Fgl2

As the present inventor was the first to identify the immunosuppressive activity of soluble fgl2, the present invention relates to all such uses of soluble fgl2 including the therapeutic and diagnostic methods and pharmaceutical compositions which are described herein below.

In all embodiments of the invention, the term "soluble fgl2 protein" means a non-membrane bound fgl2 protein including soluble fgl2 from any species or source and includes analogs and fragments or portions of a soluble fgl2 protein. Soluble fgl2 proteins (or analogs, fragments or portions thereof) of the invention are those that are able to suppress an immune response and preferably inhibit T cell proliferation. The soluble fgl2 proteins may have no prothrombinase activity.

Determining whether a particular soluble fgl2 protein can suppress an immune response can be assessed using known in vitro immune assays including, but not limited to, inhibiting a mixed leucocyte reaction; inhibiting T-cell proliferation; inhibiting interleukin-2 production; inhibiting IFNγ production; inhibiting a Th1 cytokine profile; inducing IL-4 production; inducing TGFβ production; inducing IL-10 production; inducing a Th2 cytokine profile; inhibiting immunoglobulin production; altering serum immunoglobulin isotype profiles (from those associated with Th1 type immunity—e.g. in the mouse, IgG1 and IgG2a, to those associated with Th2 type immunity—e.g. in the mouse, IgG2b, IgG3); inhibition of dendritic cell maturation; and any other assay that would be known to one of skill in the art to be useful in detecting immune suppression.

The soluble fgl2 protein may be obtained from known sources or prepared using known techniques such as recombinant or synthetic technology. The protein may have any of the known published sequences for fgl2 which can be obtained from public sources such as GenBank. Examples of such sequences include, but are not limited to Accession Nos. AAL68855; P12804; Q14314; $NPO_{32039}$; AAG42269; AAD10825; AAB88815; AAB88814; NP006673; MC16423; AAC16422; AAB92553. The fgl2 sequences can also be found in WO 98/51335 (published Nov. 19, 1998) and in Marazzi et al. (1998), Rüegg et al. (1995) and Yuwaraj et al. (2001) (17, 18, 41)). The aforementioned sequences are incorporated herein by reference. The soluble fgl2 protein can be obtained from any species, preferably a mammal including human and mouse.

The term "analog" as used herein includes any peptide having an amino acid sequence that is similar to any of the known soluble fgl2 sequences in which one or more residues have been substituted with a functionally similar residue and which displays the ability to suppress an immune response. Analogs include conservative substitutions, derivatives, peptide mimetics and homologs of soluble fgl2. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" as used herein refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5 hydroxylysine may be substituted for lysine; 3-methylhistidine may be substituted for histidine; homoserine may be substituted for serine; and ornithine may be substituted for lysine.

The term "peptide mimetic" as used herein includes synthetic structures which may or may not contain amino acids and/or peptide bonds but retain the structural and functional features of a soluble fgl2 protein or peptide. Peptide mimetics also include peptoids, oligopeptoids; and peptide libraries containing peptides of a designed length representing all possible sequences of amino acids corresponding to a soluble fgl2 protein. Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The soluble fgl2 protein may be modified to make it more therapeutically effective or suitable. For example, the soluble fgl2 protein may be cyclized as cyclization allows a peptide to assume a more favourable conformation. Cyclization of the soluble fgl2 peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the soluble fgl2 protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

Fragments or portions of the soluble fgl2 protein include fragments or portions of the known fgl2 sequences as well as fragments or portions of analogs of soluble fgl2. The inventor has shown that full length mRNA transcripts of fgl2 (1.3 kb) are made in antigen presenting cells and naïve T cells. The inventor has also shown that 5' truncated fgl2 mRNA transcripts are present in Con-A stimulated T cells, indicating that activated T cells secrete truncated fgl2 proteins that are devoid of a transmembrane domain. The sequence of 3 truncated soluble fgl2 molecules is provided in FIGS. 12-14 and SEQ ID NOS:1-6. The sequences of these shorter transcripts reveal that they are not splice variants but instead are truncations at the 5' end of the full length transcripts, indicating they are the products of alternative transcriptional start sites. The predicted amino acid sequence of the longest open reading frame (indicated by Kozak consensus translational start site) of these truncated transcripts corresponds to truncated fgl2 proteins that are devoid of the hydrophobic region, which can serve as a transmembrane domain. Thus, these truncated fgl2 proteins can account for the soluble fgl2 protein secreted by T cells. Since the hydrophobic region of fgl2 overlap with its signal peptide sequence, the putative truncated fgl2 protein will lack the signal peptide necessary for the classical endoplasmic reticulum-golgi secretion pathway. Therefore, all of the truncated proteins lack the hydrophobic region and the signal peptide sequence present in the full length fgl2 protein. Accordingly, in one embodiment a truncated soluble fgl2 protein useful in the present invention lacks the hydrophobic region of full length fgl2. The inventor has also shown that exon 2, but not exon 1, of fgl2 is necessary for the immunosuppressive activity of soluble fgl2. Accordingly, in another embodiment, the soluble fgl2 protein useful in the present invention comprises the amino acid sequence encoded by exon 2 of the fgl2 gene.

In one embodiment, the soluble fgl2 protein (i) is encoded by a nucleic acid molecule shown in SEQ ID NO:1 (FIG. 12A); (ii) has the amino acid sequence shown in SEQ ID NO:2 (FIG. 12B); or (iii) is an analog of (i) or (ii).

In another embodiment, the soluble fgl2 protein (i) is encoded by a nucleic acid molecule shown in SEQ ID NO:3 (FIG. 13A); (ii) has the amino acid sequence shown in SEQ ID NO:4 (FIG. 13B); or (iii) is an analog of (i) or (ii).

In yet another embodiment, the soluble fgl2 protein (i) is encoded by a nucleic acid molecule shown in SEQ ID NO:5 (FIG. 14A); (ii) has the amino acid sequence shown in SEQ ID NO:6 (FIG. 14B); or (iii) is an analog of (i) or (ii).

The present invention also includes isolated nucleic acid molecules encoding a soluble fgl2 protein.

The term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

In one embodiment, the nucleic acid molecule encoding soluble fgl2 comprises exon 2 of the fgl2 gene.

In a preferred embodiment, the nucleic acid molecule encoding soluble fgl2 protein comprises:

(a) a nucleic acid sequence as shown in FIG. 12A (SEQ ID NO:1) or 13A (SEQ ID NO:3) or 14A (SEQ ID NO:5) wherein T can also be U;

(b) a nucleic acid sequence that is complimentary to a nucleic acid sequence of (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner and encode a soluble fgl2 protein that is capable of suppressing an immune response. The variations may be attributable to local mutations or structural modifications. Nucleic acid sequences having substantial homology include nucleic acid sequences having at least 65%, more preferably at least 85%, and most preferably 90-95% identity with the nucleic acid sequences as shown in FIG. 12A (SEQ ID NO:1) or 13A (SEQ ID NO:3) or 14A (SEQ ID NO:5).

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the sequence of (a) (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in FIG. 12A (SEQ ID NO:1) or 13A (SEQ ID NO:3) or 14A (SEQ ID NO:5) with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain: alkyl or cycloalkyl intersugar linkages or short chain heteroatomic or heterocyclic intersugar linkages in the nucleic acid molecule shown in FIG. 12A (SEQ ID NO:1) or 13A (SEQ ID NO:3) or 14A (SEQ ID NO:5). For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replace with a polyamide backbone which is similar to that found in peptides (P. E. Nielsen et al, Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

II. Therapeutic Methods

In one aspect, the present invention provides a method of suppressing an immune response comprising administering an effective amount of a soluble fgl2 protein or a nucleic acid sequence encoding a soluble fgl2 protein to an animal in need of such treatment. The invention also includes a use of an effective amount of a soluble fgl2 protein or a nucleic acid sequence encoding a soluble fgl2 protein to suppress an immune response or in the manufacture of a medicament to suppress an immune response.

The term "administering a soluble fgl2 protein" includes both the administration of a soluble fgl2 protein (as defined above) as well as the administration of a nucleic acid sequence encoding a soluble fgl2 protein. In the latter case, the soluble fgl2 protein is produced in vivo in the animal.

Administration of an "effective amount" of the soluble fgl2 protein and nucleic acid of the present invention is defined as an amount effective, at dosages and for periods of time necessary to achieve the desired result, for example suppression of an immune response. The effective amount of the soluble fgl2 protein or nucleic acid of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

The term "suppress" or "reduce" or "inhibit" a function or activity, such as an immune response, means to suppress or reduce the function or activity when compared to otherwise same conditions in the absence of soluble fgl2.

The term "animal" as used herein includes all members of the animal kingdom including humans.

As mentioned previously, the inventor has shown that soluble fgl2 inhibits T-cell proliferation, prevents DC maturation and promotes Th2 cytokine expression.

In one embodiment, the present invention provides a method of preventing or inhibiting T-cell proliferation comprising administering an effective amount of a soluble fgl2 protein or a nucleic acid sequence encoding a soluble fgl2 protein to an animal in need thereof. The invention includes a use of an effective amount of a soluble fgl2 protein or a nucleic acid sequence encoding a soluble fgl2 protein to prevent or inhibit T-cell proliferation or in the manufacture of a medicament to prevent or inhibit T-cell proliferation.

In another embodiment, the present invention provides a method of preventing or inhibiting DC maturation comprising administering an effective amount of a soluble fgl2 protein or a nucleic acid sequence encoding a soluble fgl2 protein to an animal in need thereof. The invention includes a use of an effective amount of a soluble fgl2 protein or a nucleic acid sequence encoding a soluble fgl2 protein to prevent or inhibit DC maturation or in the manufacture of a medicament to prevent or inhibit DC maturation.

In a further embodiment, the present invention provides a method of promoting a Th2 cytokine response comprising administering an effective amount of a soluble fgl2 protein or a nucleic acid sequence encoding a soluble fgl2 protein to an animal in need thereof. The invention includes a use of an effective amount of a soluble fgl2 protein or a nucleic acid sequence encoding a soluble fgl2 protein to promote a Th2 cytokine response or in the manufacture of a medicament to promote a Th2 cytokine response.

The term "promoting a Th2 cytokine response" means that the levels of Th2 cytokines is enhanced, increased or induced as compared to the levels observed in the absence of soluble fgl2. Th2 cytokines include, but are not limited to, IL-4 and IL-10. It is known that promoting a Th2 cytokine response is helpful in treating a number of conditions requiring immune suppression.

In another aspect of the present invention, there is provided a method of treating a disease or condition wherein it is desirable to suppress an immune response comprising administering an effective amount of a soluble fgl2 protein or a nucleic acid sequence encoding a soluble fgl2 protein to an animal in need of such treatment. The invention also includes a use of an effective amount of a soluble fgl2 protein or a nucleic acid sequence encoding a soluble fgl2 protein to treat a disease or condition wherein it is desirable to suppress an immune response or in the manufacture of a medicament to suppress an immune response.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The method of the invention may be used to treat any disorder or condition wherein it is desirable to suppress an immune response, for example, to induce immune suppression of tolerance to transplanted organs or tissues, treating graft versus host disease, treating autoimmune diseases and treating allergies.

As stated hereinabove, the findings that soluble fgl2 inhibited T-cell proliferation, promoted Th2 cytokine expression and prevented DC maturation suggest a novel usage of soluble fgl2 protein as an immunosuppressive agent which may induce T-cell tolerance and therefore improve allograft survival. Accordingly, in an embodiment of the present invention, there is provided a method of suppressing an immune response to a transplanted organ or tissue in a recipient animal comprising administering an effective amount of a soluble fgl2 protein or a nucleic acid sequence encoding a soluble fgl2 protein to the recipient animal. The soluble fgl2 can be administered prior to, during or after the transplantation of the organ or tissue. The invention includes a use of an effective amount of a soluble fgl2 protein or a nucleic acid sequence encoding a soluble fgl2 protein to induce immune suppression or tolerance to a transplanted organ or tissue or in the manufacture of a medicament to induce immune suppression or tolerance to a transplanted organ or tissue.

The term "inducing immune tolerance" means rendering the immune system unresponsive to a particular antigen without inducing a prolonged generalized immune deficiency. The term "antigen" means a substance that is capable of inducing an immune response. In the case of transplantation, immune tolerance means rendering the immune system unresponsive to the antigens on the transplant. In the case of autoimmune disease, immune tolerance means rendering the immune system unresponsive to an auto-antigen that the host is recognizing as foreign, thus causing an autoimmune response. In the case of allergy, immune tolerance means rendering the immune system unresponsive to an allergen that generally causes an immune response in the host. An alloantigen refers to an antigen found only in some members of a species, such as blood group antigens. A xenoantigen refers to an antigen that is present in members of one species but not members of another. Correspondingly, an allograft is a graft between members of the same species and a xenograft is a graft between members of a different species.

The recipient can be any member of the animal kingdom including rodents, pigs, cats, dogs, ruminants, non-human primates and preferably humans. The organ or tissue to be transplanted can be from the same species as the recipient (allograft) or can be from another species (xenograft). The tissues or organs can be any tissue or organ including heart, liver, kidney, lung, pancreas, pancreatic islets, brain tissue, cornea, bone, intestine, skin and haematopoietic cells.

The method of the invention may also be used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example.

Accordingly, in another embodiment, the present invention provides a method of preventing or inhibiting graft versus host disease in a recipient animal receiving an organ or tissue transplant comprising administering an effective amount of a soluble fgl2 protein or a nucleic acid sequence encoding a soluble fgl2 protein to the organ or tissue prior to the transplantation in the recipient animal. The invention includes a use of an effective amount of a soluble fgl2 protein or a nucleic acid molecule encoding a soluble fgl2 protein to prevent or inhibit graft versus host disease or in the manufacture of a medicament to prevent or inhibit graft versus host disease.

As stated previously, the method of the present invention may also be used to treat or prevent autoimmune disease. In an autoimmune disease, the immune system of the host fails to recognize a particular antigen as "self" and an immune reaction is mounted against the host's tissues expressing the antigen. Normally, the immune system is tolerant to its own host's tissues and autoimmunity can be thought of as a breakdown in the immune tolerance system.

Accordingly, in a further embodiment, the present invention provides a method of preventing or treating an autoimmune disease comprising administering an effective amount of a soluble fgl2 protein, or a nucleic acid sequence encoding a soluble fgl2 protein to an animal having, suspected of having, or susceptible to having an autoimmune disease. The invention includes a use of an effective amount of a soluble fgl2 protein on a nucleic acid molecule encoding a soluble fgl2 protein to prevent or inhibit an autoimmune disease or in the manufacture of a medicament to prevent or inhibit an autoimmune disease.

Autoimmune diseases that may be treated or prevented according to the present invention include, but are not limited to, arthritis, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

One of skill in the art can determine whether or not a particular soluble fgl2, or fragment thereof, is useful in preventing autoimmune disease. As mentioned previously, one of skill in the art can readily test a soluble fgl2 or a soluble fgl2 fragment for its ability to suppress an immune response using known in vitro assays. In addition the soluble fgl2 or a soluble fgl2 fragment can also be tested for its ability to prevent autoimmune in an animal model. Further, many other autoimmune animal models are available, including, but not limited to, experimental allergic encephalomyelitis which is an animal model for multiple sclerosis, animal models of inflammatory bowel disease (induced by immunization, or developing in cytokine-knockout mice), and models of autoimmune myocarditis and inflammatory eye disease.

As stated previously, the method of the present invention may also be used to treat or prevent an allergic reaction. In an allergic reaction, the immune system mounts an attack against a generally harmless, innocuous antigen or allergen. Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

Accordingly, in a further embodiment, the present invention provides a method of preventing or treating an allergy comprising administering an effective amount of a soluble fgl2 protein or a nucleic acid sequence encoding a soluble fgl2 protein to an animal having or suspected of having an allergy. The invention includes a use of an effective amount of a soluble fgl2 protein or a nucleic acid molecule encoding a soluble fgl2 protein to prevent or treat an allergy.

III. Compositions

The invention also includes pharmaceutical compositions containing soluble fgl2 proteins or nucleic acids encoding a soluble fgl2 protein for use in immune suppression.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as immunosuppressive drugs or antibodies to enhance immune tolerance or immunostimulatory agents to enhance the immune response.

The present invention provides a pharmaceutical composition for use in suppressing an immune response comprising an effective amount of a soluble fgl2 protein in admixture with a pharmaceutically acceptable diluent or carrier.

In one embodiment, the pharmaceutical composition for use in preventing graft rejection comprises an effective amount of a soluble fgl2 protein in admixture with a pharmaceutically acceptable diluent or carrier.

In another embodiment, the pharmaceutical composition for use in preventing graft rejection comprises an effective amount of a nucleic acid molecule encoding a soluble fgl2 protein in admixture with a pharmaceutically acceptable diluent or carrier.

The nucleic acid molecules of the invention encoding a soluble fgl2 protein may be used in gene therapy to induce immune tolerance. Recombinant molecules comprising a nucleic acid sequence encoding a soluble fgl2 protein, or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells.

IV. Diagnostic Methods

The finding by the present inventor that soluble fgl2 is involved in immune suppression allows development of diagnostic assays for detecting diseases associated with immune suppression.

Accordingly, the present invention provides a method of detecting a condition associated with immune suppression comprising assaying a sample for (a) a nucleic acid molecule encoding a soluble fgl2 protein or a fragment thereof or (b) a soluble fgl2 protein or a fragment thereof.

To detect nucleic acid molecules encoding soluble fgl2 nucleotide probes can be developed to detect soluble fgl2 or fragments thereof in samples, preferably biological samples such as cells, tissues and bodily fluids. The probes can be useful in detecting the presence of a condition associated with soluble fgl2 or monitoring the progress of such a condition. Such conditions include the status of a transplant or an autoimmune disease. Accordingly, the present invention provides a method for detecting a nucleic acid molecules encoding a soluble fgl2 comprising contacting the sample with a nucleotide probe capable of hybridizing with the nucleic acid molecule to form a hybridization product, under conditions which permit the formation of the hybridization product, and assaying for the hybridization product.

Example of probes that may be used in the above method include fragments of the nucleic acid sequences shown in SEQ ID NOS:1-6. A nucleotide probe may be labelled with a detectable substance such as a radioactive label which provides for an adequate signal and has sufficient half-life such as 32P, 3H, 14C or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that hybridize to the nucleic acid molecule of the present invention preferably, nucleic acid molecules which hybridize to the nucleic acid molecule of the invention under stringent hybridization conditions as described herein.

Soluble fgl2 protein may be detected in a sample using antibodies that bind to the protein. Antibodies to soluble fgl2 proteins may be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')2) and recombinantly produced binding partners.

Accordingly, the present invention provides a method for detecting a soluble fgl2 protein comprising contacting the sample with an antibody that binds to soluble fgl2 which is capable of being detected after it becomes bound to the soluble fgl2 in the sample.

Antibodies specifically reactive with soluble fgl2, or derivatives thereof, such as enzyme conjugates or labeled derivatives, may be used to detect soluble fgl2 in various biological materials, for example they may be used in any known immunoassays which rely on the binding interaction between an antigenic determinant of soluble fgl2, and the antibodies. Examples of such assays are radioimmunoassays, enzyme immunoassays (e.g. ELISA), immunofluorescence, immunoprecipitation, latex agglutination, hemagglutination and histochemical tests. Thus, the antibodies may be used to detect and quantify soluble fgl2 in a sample in order to determine its role in particular cellular events or pathological states, and to diagnose and treat such pathological states.

Accordingly, the invention provides a method for diagnosing a condition related soluble fgl2 expression or activity using an antibody to soluble fgl2. In one embodiment, said method comprises obtaining a biological sample from a patient (such as a blood or tissue sample) and incubating said sample with an antibody for soluble fgl2, preferably a monoclonal antibody, under conditions that permit formation of a soluble fgl2/antibody complex. Said method permits the detection and/or determination of the presence and or level of soluble fgl2 in the sample, the presence or particular level of soluble fgl2 being indicative of a soluble fgl2 related condition. In another embodiment, said antibody is a labelled antibody. In another embodiment, the amount of soluble fgl2 is determined by the amount of complexed soluble fgl2 with said soluble fgl2, either directly or indirectly. For instance, if a particular amount of antibody is used, then the amount of complexed or remaining uncomplexed (or free) antibody can be measured to infer the amount of soluble fgl2 present in the sample.

The following non-limiting examples are illustrative of the present invention:

EXAMPLES

Materials and Methods

Mice

Female 6- to 8-wk-old BALB/c (H-$2^d$) and AJ (H-$2^a$) mice were purchased from Charles River Laboratory (Wilmington, Mass.) and Jackson Laboratory (Bar Harbor, Me.), respectively. All mice were chow-fed and allowed to acclimatize for a week prior experiments.

Reagents

Recombinant mouse (rm) GM-CSF and rm IL-4 were purchased from Cedarlane Laboratories Ltd. (Hornby, ON). LPS (*Escherichia coli*), human fibrinogen and Con A were purchased from Sigma (St. Louis, Mo.). FITC- or PE-conjugated monoclonal antibodies used to detect cell surface expression of CD80 (16-10A1), CD86 (GL1), CD40 (3/23) and CD11c (HL3), MHC class I (H2-$K^d$), and MHC class II (1-$A^d$) were purchased from PharMingen (San Diego, Calif.). Anti-Thy-1.2, anti-Ly-2.2 antibodies and rabbit anti-mouse complement were purchased from Cedarlane Laboratories Ltd. All culture reagents were purchased from Life Technologies (Mississauga, ON) unless otherwise stated.

Production of Purified Soluble Fgl2 Protein

Mouse soluble fgl2 protein with a tandem repeat of six histidine residues followed by an enterokinase cleavage site fused to its N-terminus was expressed in an Invitrogen Insect Expression System (20). Briefly, a 1.4 kb cDNA encoding mouse fgl2 was amplified using the forward primer 5'-TGCCGCACTGGATCCATGAGGCTTCCTGGT-3' (SEQ ID NO:7) (with the methionine start codon underlined) and the reverse primer 5'-TTATGGCTTGAAATTCTTGGGC-3' (SEQ ID NO:8) (nt 1283 to 1302 relative to the ATG start codon). Amplification was performed for 25 cycles with 2 min at 96° C., 2 min at 55° C. and 3 min at 72° C. The PCR product was cloned into the EcoR1 and BamH1 sites of the vector pBlueBacHis2A (Invitrogen).

Putative recombinant viruses were generated according to the Invitrogen protocol and screened for the presence of fgl2 by PCR followed by three rounds of viral plaque purification. The sequence of the recombinant baculovirus containing mouse fgl2 cDNA was confirmed by an automated DNA sequencer (Applied Biosystems, model 377, Perkin-Elmer).

Monolayers of High 5 insect cells were infected with the recombinant baculovirus for the expression of mouse fgl2 protein. Seventy-two hours later, the infected cells were harvested by centrifugation and lysed in 6 M guanidinium hydrochloride, 20 mM sodium phosphate and 500 mM NaCl. The soluble material was mixed with 50% slurry of ProBond Nickel-NTA (Ni-NTA) resin (Invitrogen) for 1 h at 4° C. After washings, bound fgl2 protein was eluted with 8 M urea, 20 mM sodium phosphate, pH 5.3 with 150 mM NaCl. The pH of the eluted protein was adjusted to pH 7.2 immediately upon elution, and the protein was renatured by dialyzing against urea-saline buffers (150 mM NaCl, pH 7.2) with successive decreases in urea concentrations (6M, 4M, 2M, 1M) and finally against Tris-buffered saline (10 mM Tris, 150 mM NaCl, pH 7.2). The dialyzed material was concentrated and soluble fgl2 protein was collected by centrifugation at 14,000 rpm for 10 min to remove insoluble particulates. Protein concentrations were determined by a modified Lowry method, Bicinchoninic Acid (BCA) assay (Pierce; Brockville, ON).

Homogeneity of purified soluble fgl2 protein was evaluated by SDS-PAGE and confirmed by Western blot probed with anti-fgl2 antibody as previously described (16). Proteins were stained directly using Coomassie brilliant blue or were transferred to nitrocellulose, and probed using polyclonal rabbit anti-mouse fgl2 IgG as the primary Ab. The secondary Ab utilized for immunoblotting was affinity-purified donkey anti-rabbit IgG conjugated to horseradish peroxidase (Amersham, Buckinghamshire, UK) and the blot was visualized with an immunochemiluminescent kit (Amersham).

Biotinylation of Soluble Fgl2 and Bovine Serum Albumin (BSA)

A 1 mg/ml solution of purified soluble fgl2 and Ig-free BSA (Sigma) were incubated with a 1:10 molar reaction mixture of D-Biotinyl-ϵ-aminocaproic acid-N-hydroxy-succinimide ester (Biotin-7-NHS) (Roche Diagnostics, Laval, QC) for 1 h at room temperature with gentle mixing. The reaction was then applied to a Sephadex G-25 column (Roche Diagnostics), washed with 1.5 ml of PBS, then the biotinylated-soluble fgl2 was eluted with 3.5 ml of PBS. The eluate was collected and the protein concentration was determined by a modified Lowry method, Bicinchoninic Acid (BCA) assay. The labeled proteins were utilized in binding assays as described below.

Preparation of Cells

Spleen, lymph node and bone marrow cell suspensions were prepared aseptically. Spleen mononuclear cells were isolated by standard Lympholyte-M density gradient (Cedarlane). All cell suspensions were resuspended in complete medium (α-MEM, supplemented with 10% FBS, 50 μM β-mercaptoethanol, 1 mM $_L$-glutamine, 100 U/ml penicillin and 100 mg/ml streptomycin).

Bone marrow-derived DC were prepared as described elsewhere (21). Briefly, bone marrow cells were removed from femurs and tibias of BALB/c (H-$2^d$) mice and filtered through nylon mesh. Cells were incubated with anti-Thy-1.2 on ice for 45 min and then treated with rabbit anti-mouse complement for an h at 37° C. The cells were washed and cultured in 100 mm tissue culture dishes in complete medium supplemented with 10% FBS (Flow Laboratories, Mississauga, Canada) at a concentration of $1\times10^6$ cells/ml with recombinant mouse (rm) GM-CSF (800 U/ml) and rm IL-4 (500 U/ml). On day 2 and 4, nonadherent granulocytes were discarded and fresh rm GM-CSF and rm IL-4 were added at 36-h intervals. Immature DC were collected on day 7 and LPS (1 μg/ml) was added to the culture for 24 h to allow for maturation.

Assays for T Cell Proliferation

All assays were performed in 96-well U-bottom microtiter plates (Falcon Plastics, NJ) in a humidified atmosphere with 5% $CO_2$ at 37° C.

1. Alloantigen Stimulation

For alloantigen stimulation, Balb/c splenic mononuclear cells ($4\times10^5$ cells/100 μl) were stimulated with irradiated (3000 rad) A/J splenic mononuclear cells ($4\times10^5$ cells/100 μl) with or without soluble fgl2 protein (ranging from 1 μg/ml to 1 ng/ml) added to the culture.

2. Response to Concanaviin A (Con A)

Purified T cells ($2\times10^5$ cells/200 μl) were stimulated with Con A (5 μg/ml; Sigma) in the presence or absence of soluble fgl2 protein (ranging from 1 μg/ml to 1 ng/ml). After 3 d, cells were pulsed with [$^3$H]thymidine (1 μCi/well) (Amersham Biosciences; Piscataway, N.J.) for 18 h prior to harvesting and determining the incorporated radioactivity.

3. Response to Anti-CD3 and Anti-CD28

Purified T cells ($2\times10^5$ cells/200 μl) were stimulated with immobilized anti-CD3 mAb (1 μg/ml) and soluble anti-CD28 mAb (20 ng/ml) in the presence or absence of soluble fgl2 protein (ranging from 1 μg/ml to 1 ng/ml). After 3 d, cells were pulsed with [$^3$H]thymidine (1 μCi/well) (Amersham Biosciences; Piscataway, N.J.) for 18 h prior to harvesting and determining the incorporated radioactivity.

H5 supernatants, wild type baculovirus infected H5 supernatants, human fibrinogen (1 μg/ml) and bovine serum albumin (1 μg/ml) were added to the culture in parallel with soluble fgl2 protein as controls as previously described (20).

In some experiments, a monoclonal Ab against the "domain 2" (FRED-containing C terminal region) of fgl2 (1 μg) was added at the beginning of culture along with soluble fgl2 protein. An isotype control Ab was added for comparison.

Allogeneic Mixed Leukocyte Reaction

DC ($1\times10^4$) obtained from the bone marrow of A/J mice were first stimulated with LPS as described above, irradiated and then were mixed with responder BALB/c lymph node T cells ($2\times10^5$) in 96-well U-bottom microtiter plates for 48 h. Purified soluble fgl2 protein (1 μg/ml or 1 ng/ml) was added at the beginning of cultures. Proliferation was measured by pulsing after 2 d of culture with [$^3$H]thymidine (1 μCi/well) for 18 h as described above. In cultures used to assess cytokine production, supernatants were pooled from triplicate wells at 40 h. Levels of IL-2, IL-4, IFN-γ, and IL-10 were assayed using ELISA kits (Pierce) according to the manufacturer's instructions. Where CTL induction was assayed, cultures were allowed to continue for 5 days (in the presence/absence of soluble fgl2), before cells were harvested. These effector cells were assayed in standard 4 hr $^{51}$Cr-release assays at various effector:target ratios with $^{51}$Cr-labeled 72 hr-Con A activated A/J blast target cells, as described elsewhere (21). Data were expressed as a percent specific lysis at 50:1 effector:target.

The effect of soluble fgl2 on the LPS-induced maturation of BM-derived DC was examined by adding soluble fgl2 protein (1 μg/ml) to DC cultures during LPS-induced maturation. The treated DC cultures were then washed and examined for their ability to stimulate alloreactive T cell proliferation as described above. The expression of surface molecules including CD40, CD80, CD86, CD11c, MHC class I and class II molecules were measured by flow cytometric analysis. In other experiments, lymph node T cells were exposed to soluble fgl2 protein (1 μg/ml) for 12 h, washed then cultured with allogeneic DC. Proliferation was measured by pulsing after 2 days of culture with [$^3$H]thymidine (1 μCi/well) for 18 h as described above.

One-Way Xenogeneic Mixed Lymphocyte Reaction (MLR)

Female Wistar rats (150 g, Charles River, Wilmington, Mass.) were used as xenogeneic skingraft donors that were engrafted onto Balb/c mice for 13 days prior to being sacrificed. Then, splenic mononuclear cells ($1\times10^6$ cells/100 μl) from skingraft recipients were harvested as responder cells and restimulated in vitro with irradiated (3000 rad) Wistar splenic mononuclear cells ($1\times10^6$ cells/100 μl) in 96-well U-bottom microtiter plates with or without purified soluble fgl2 protein (from 0.1 μg/ml to 1 μg/ml). The culture was incubated at 5% $CO_2$, and 37° C. for 3 days and then the cells were pulsed with of [$^3$H] thymidine (1 μCi/well) (Amersham) for 18 hr before harvesting. Cell proliferation was quantified by [$^3$H] thymidine incorporation using a TopCount β-counter (Canberra-Packard Canada Ltd., Mississauga, ON).

Flow Cytometric Analysis

To examine the binding of biotinylated-soluble fgl2 to peripheral T cells or BM-derived DC, cells were washed twice with PBS, blocked with 10% v/v normal mouse serum for 5 min at room temperature and then incubated with biotinylated-soluble fgl2 protein in PBS at 4° C. for 30 min. Cells were washed extensively, stained with SA-PE (Pharmingen) at 4° C. for 30 min then analyzed on COULTER Epics-XL-MCL flow cytometer (Beckman Coulter, Fla.) using XL software. Binding of biotinylated-soluble fgl2 on T cells and DC was analyzed on CD3- and CD11c-positive cells, respectively. Cells incubated with biotinylated-BSA then SA-PE were used as negative controls.

For characterization of the prepared DC population, $2\times10^5$ cells were first blocked with 10% v/v normal mouse serum for 5 min at room temperature and thereafter stained with the corresponding FITC- or PE-conjugated mAb in PBS with 1% BSA at 4° C. for 30 min. Cells stained with the appropriate isotype-matched Ig were used as negative controls. Cells were analyzed on COULTER Epics-XL-MCL flow cytometer for expression of various DC markers.

To assess cell cycle and apoptosis, cells treated with soluble fgl2 protein for 12 h were washed in cold PBS, resuspended in lysis buffer (0.1% sodium citrate/Triton X-100) containing 100 units/ml RNase A (Sigma) and stained with propidium iodide (PI) (1 mg/ml PBS) in the dark for 20 min at room temperature. The cells were then washed twice and approximately 10,000 data events per sample were analyzed. Gates were set, by using the untreated sample, to differentiate between $G_0/G_1$ (left-hand peak), S-phase (intermediate) and $G_2/M$ (right-hand peak). Apoptotic cells appeared to the left of the G0/G1 phase.

Immunofluorescence Microscopy

The effect of soluble fgl2 on LPS-induced NF-κB translocation was examined as previously described (22). Immature DC were harvested on day 7 and were allowed to adhere to autoclaved glass coverslips for 6 h at 37° C., 5% $CO_2$, incubated in complete medium supplemented 10% FBS, GM-CSF and recombinant mouse IL-4 as described above. To examine the effects that soluble fgl2 had on LPS-induced NF-κB translocation, soluble fgl2 protein (1 μg/ml) was added to the DC cultures during LPS (1 μg/ml) stimulation. NF-κB translocation was examined at 5, 15, 30, 60, 120, 240 min. Cells were fixed for 30 min in PBS supplemented with 2% paraformaldehyde. The coverslips were washed three times with PBS for 10 min each, permeabilized with 0.2% Triton X-100 in PBS for 5 min, and then blocked with 5% BSA in PBS for 30 min at room temperature. The samples were stained with a goat anti-p65 polyclonal antibody (1:50 dilution in PBS) (Molecular Probes Inc. Eugene, Oreg.) for 1 hr at room temperature, washed three times with PBS for 5 min each, and incubated with fluorescently labeled Alexa 555 donkey anti-goat IgG secondary antibody (1:400 dilution in PBS) (Molecular Probes Inc., Eugene, Oreg.) for 1 hr at room temperature. The coverslips were washed three times with PBS for 5 min each and mounted on glass slides using mounting solution (DAKO from Dakocytomation, Carpinteria, Calif.). Nuclei were counterstained with DAPI (4',6'-diamidino-2-phenylindole) chromosomal staining (Molecular Probes Inc, Eugene, Oreg.). The staining was visualized using a Nikon TE200 fluorescence microscope (X100 objective) coupled to Orca 100 camera driven by Simple PCI software as previously described (22).

Statistical Analysis

The results were calculated as means±standard error of the mean (SEM). For statistical comparison, the means were compared using the analysis of variance by Student's t-test using the software Statistix 7 (Analytical Software). A "p" value≦0.05 was considered statistically significant.

Example 1

Generation of Soluble Fgl2 Protein in a Baculovirus Expression System

Figure 1:
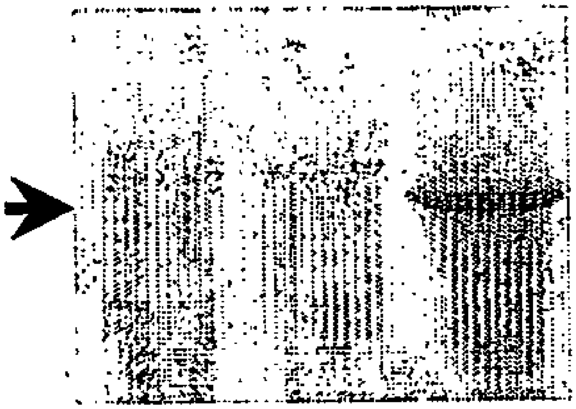
FIGS. 1A and B shows the generation of soluble fgl2 protein in a baculovirus system. SDS-PAGE followed by Coomassie blue staining of fgl2 protein purified from recombinant baculovirus-infected High 5 (H5) cells showed a dominant band at 65-kDa confirmed by (b) Western blotting. Fgl2 protein was generated using a baculovirus expression system and purified as described in the "Materials and Methods". Cell lysates prepared under denaturing condition were incubated with Ni-NTA resin and proteins bound to Ni-NTA resin were eluted. All eluted proteins (10 μg) were analyzed on 10% SDS-PAGE followed by (a) Coomassie blue staining or (b) Western blot analysis probed with polyclonal rabbit anti-mouse fgl2 IgG as described in the "Materials and Methods". Lane 1, eluted proteins from lysate of the uninfected H5 cells; lane 2, eluted proteins from lysate of the wild type baculovirus infected H5 cells; lane 3, eluted proteins from lysate of the recombinant baculovirus-infected H5 cells.
Figure 1:
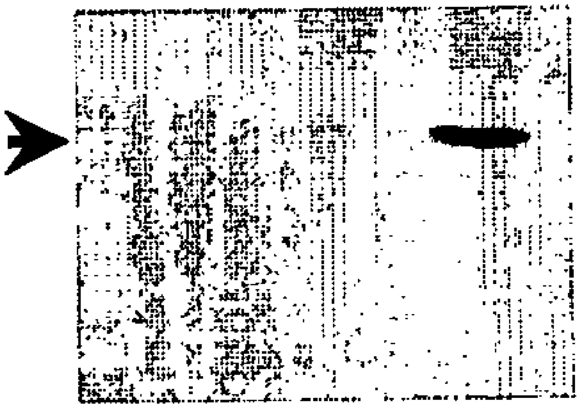

To characterize the immunomodulatory property of soluble fgl2, fgl2 protein was generated using a baculovirus expression system and purified as described in the Methods. SDS-PAGE followed by Coomassie blue staining of the purified soluble fgl2 protein showed a dominant band at 65-kDa, comparable to the size of the fgl2 protein previously reported (15, 16) (FIG. 1A). Purified soluble fgl2 was confirmed by Western blotting using polyclonal rabbit anti-mouse fgl2 IgG (FIG. 1B). The purified soluble fgl2 protein was analyzed for its ability to induce clotting and no coagulation activity was detected (data not shown).

Soluble Fgl2 Binding to T Cells and DC

Figure 2:
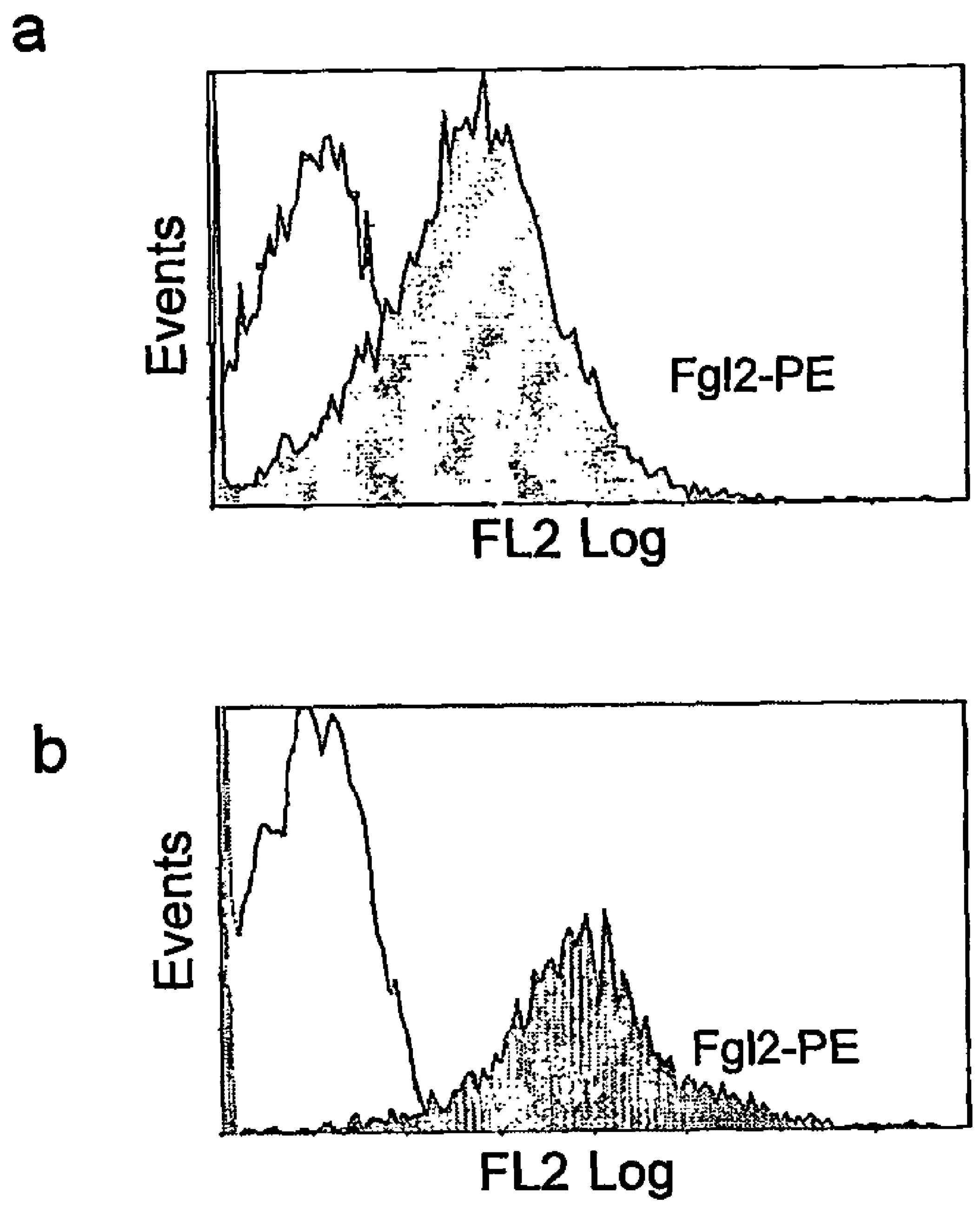
FIGS. 2A and B shows the binding of biotinylated-soluble fgl2 to T cells and BM-derived LPS-induced mature DC. T cells and BM-derived LPS-induced mature DC cells were prepared. CD3- and CD11c-positive populations were gated and the binding of soluble fgl2 to T cells (a) and dendritic cells (b) was determined as described in the "Materials and Methods" (shown in grey area). The white area shows the binding of biotinylated-BSA control.

The binding of purified soluble fgl2 to T cells and DC was examined using flow cytometry analysis. FIG. 2 shows that biotinylated-soluble fgl2 bound to both T cells and DC. The specific binding of biotinylated-soluble fgl2 to both cells was inhibited by non-biotinylated soluble fgl2 but not by fibrinogen (data not shown).

Soluble Fgl2 Inhibited T Cell Proliferation Stimulated by Various Stimuli

Figure 3:
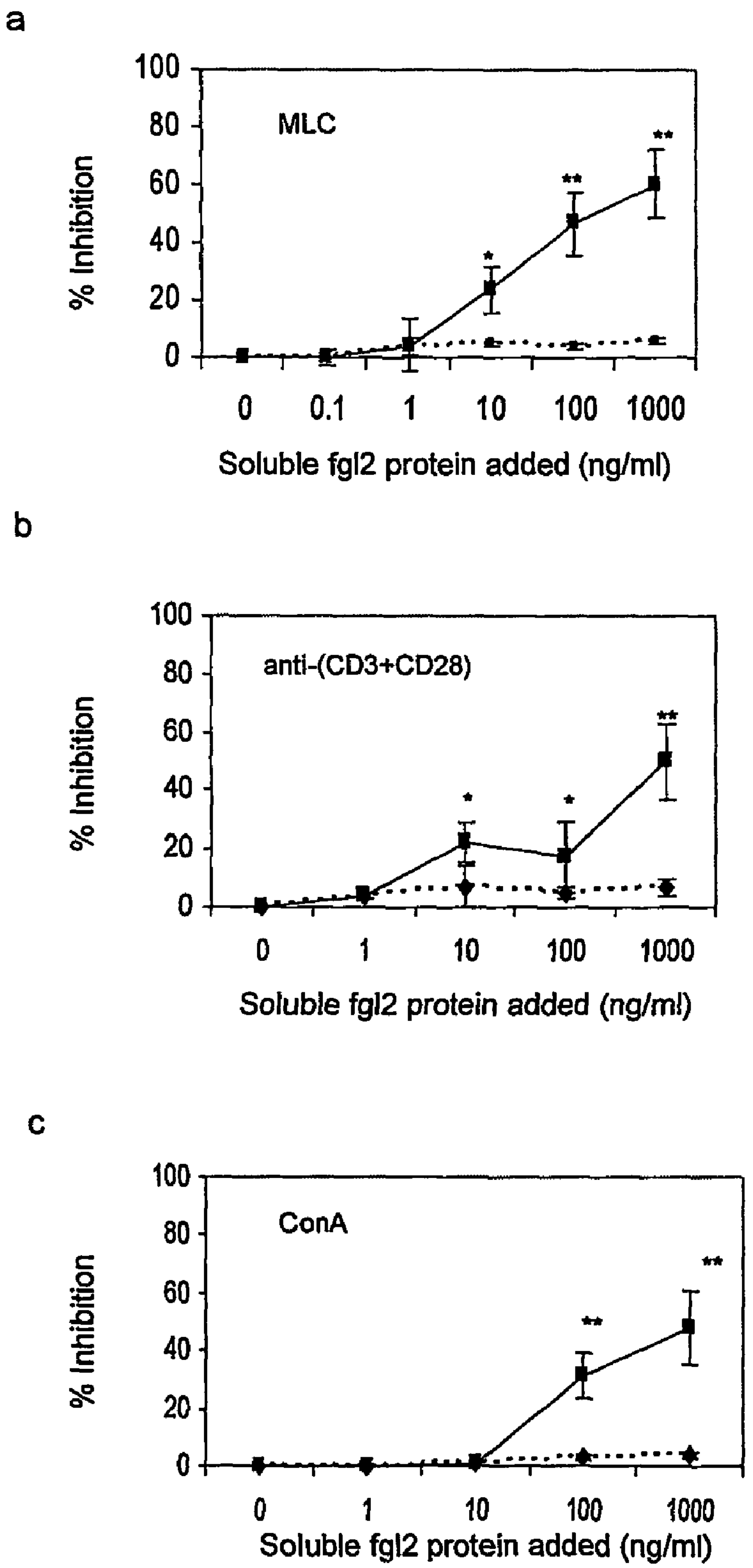
FIG. 3A-C shows the inhibitory effects of soluble fgl2 protein on T cell proliferation induced by different stimuli. Effects of soluble fgl2 protein (shown in solid line) and human fibrinogen (shown in dotted line) on T cell proliferation induced by (a) alloantigens, (b) immobilized anti-CD3 mAb (1 μg/ml) with soluble anti-CD28 mAb (20 ng/ml) and (c) Con A (5 μg/ml) with various concentrations of soluble fgl2 or human fibrinogen added at the initiation of cultures as described in the "Materials and Methods". Proliferation was determined by [$^3$H]thymidine uptake in triplicate wells and the incorporation in fgl2-untreated control cultures (shown as 0 ng/ml soluble fgl2 protein added) was as follows: (a) 14,892±978 cpm; (b) 16,890±1146 cpm; (c) 39,368±3560 cpm, with background 595±193 cpm. The data are expressed as percentage inhibition (soluble fgl2-untreated cultures shown as 0% inhibition) and are representative of three separate experiments. **, p<0.01 and *, p<0.05 compared with control groups (far left, no soluble fgl2 was added).

To examine the consequence of the binding of soluble fgl2 to T cells, purified soluble fgl2 protein was initially assessed for its capacity to inhibit T cell proliferation. FIG. 3 shows that soluble fgl2 protein inhibited allogeneic T cell activation in a dose-dependent manner. At the highest concentration of soluble fgl2 (1 μg/ml) used in the cultures, 61±11% inhibition of T cell proliferation was observed. Purified soluble fgl2 protein similarly inhibited T cell proliferation induced by immobilized anti-CD3 mAb with soluble anti-CD28 mAb and by Con A (FIG. 3*b, c*) in a dose dependent fashion. H5 supernatants, wild type baculovirus infected H5 supernatants, human fibrinogen (1 μg/ml) (FIG. 3) nor bovine serum albumin (1 μg/ml) (data not shown) had any effect on T cell proliferation stimulated by alloantigen, anti-CD3/CD28 or Con A.

Figure 4:
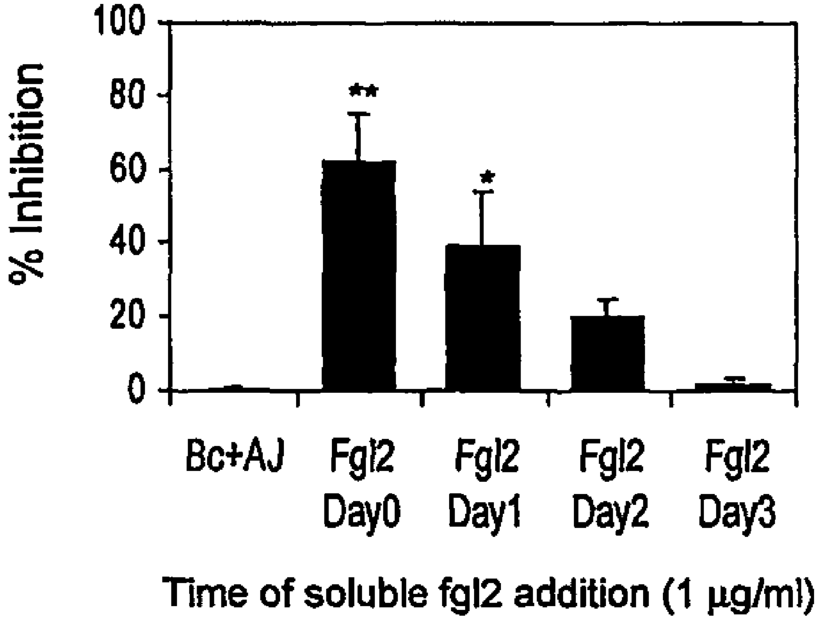
FIGS. 4A and B shows the inhibitory effect of soluble fgl2 on alloreactive T cell proliferation. (a) Kinetics of the effect of soluble fgl2 on alloreactive T cell proliferation. soluble fgl2 (1 μg/ml) was added on d 0 to d 3 to an ongoing allogeneic reaction as described in the "Materials and Methods". Proliferation was determined by [$^3$H]thymidine uptake in triplicate wells and the incorporation in soluble fgl2-untreated control cultures (shown as Bc+AJ) was: 14,892±978 cpm with background 523±102 cpm. The data are expressed as percentage inhibition (soluble fgl2-untreated cultures shown as 0% inhibition) and are representative of three separate experiments. **, p<0.01 and *, p<0.05 compared with control groups for both % suppression and cpm (far left, no soluble fgl2 was added). (b) The inhibitory effect of soluble fgl2 protein on alloreactive T cell proliferation was neutralized by an anti-mouse fgl2 mAb. One-way MLC was set up as described previously and a monoclonal anti-mouse fgl2 Ab (1 μg) was added at the beginning of cultures along with the addition of soluble fgl2 protein (1 μg/ml). An isotype control mAb was added for comparison. **, p<0.01 compared with control groups (second left, no anti-mouse fgl2 Ab added).
Figure 4:
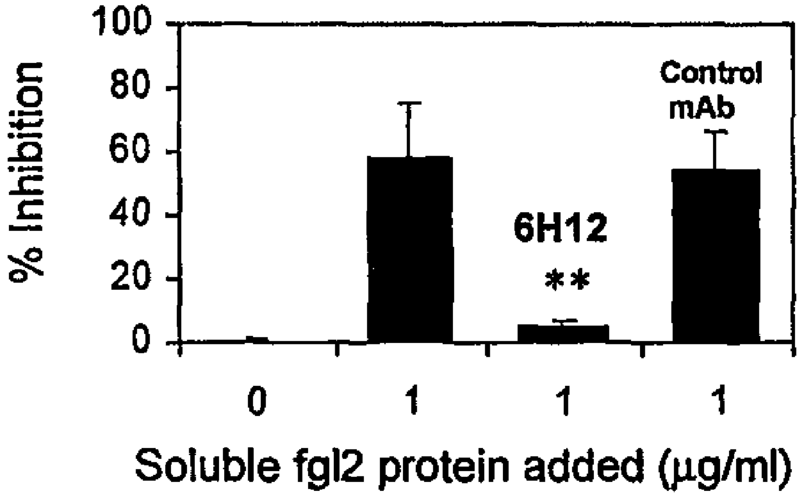

Soluble Fgl2 Inhibited Allogeneic Response at Early Time Points and the Effect could be Neutralized by Monoclonal Antibody To further explore the suppressive effect of soluble fgl2 on alloreactive T cell proliferation, soluble fgl2 protein was added to allogeneic cultures at different time points (i.e. day 0, 1, 2 or 3) and mixed by pipetting to ensure proper distribution of protein to the cultures. Cell proliferation was measured as previously described. Cultures without the addition of soluble fgl2 were also mixed by pipetting at corresponding time points as controls. FIG. 4*a* shows that soluble fgl2 exhibited maximal inhibitory effect (61±11% inhibition) when it was added at the initiation of allogeneic reactions (day 0). Less inhibitory effects were observed when soluble fgl2 was added on day 1 (39±15% inhibition) with loss of inhibition when addition of soluble fgl2 was delayed until day 2.

The ability of a monoclonal antibody (mAb) against the "domain 2" (FRED-containing C terminal region) of mouse fgl2 to neutralize the inhibitory effect of soluble fgl2 on alloreactive T cell proliferation was next examined. As shown in FIG. 4*b*, a mouse mAb (1 μg/ml) abrogated the ability of soluble fgl2 to suppress alloreactive T cell proliferation, suggesting that the effect of soluble fgl2 protein was specific and could be prevented by this Ab. In contrast, a rabbit polyclonal Ab against the "domain 1" of fgl2 which neutralizes the coagulation activity of fgl2 failed to inhibit the immunosuppressive activity of soluble fgl2 protein.

Soluble Fgl2 Promoted a Th2 Cytokine Profile in Allogeneic Responses

Figure 5:
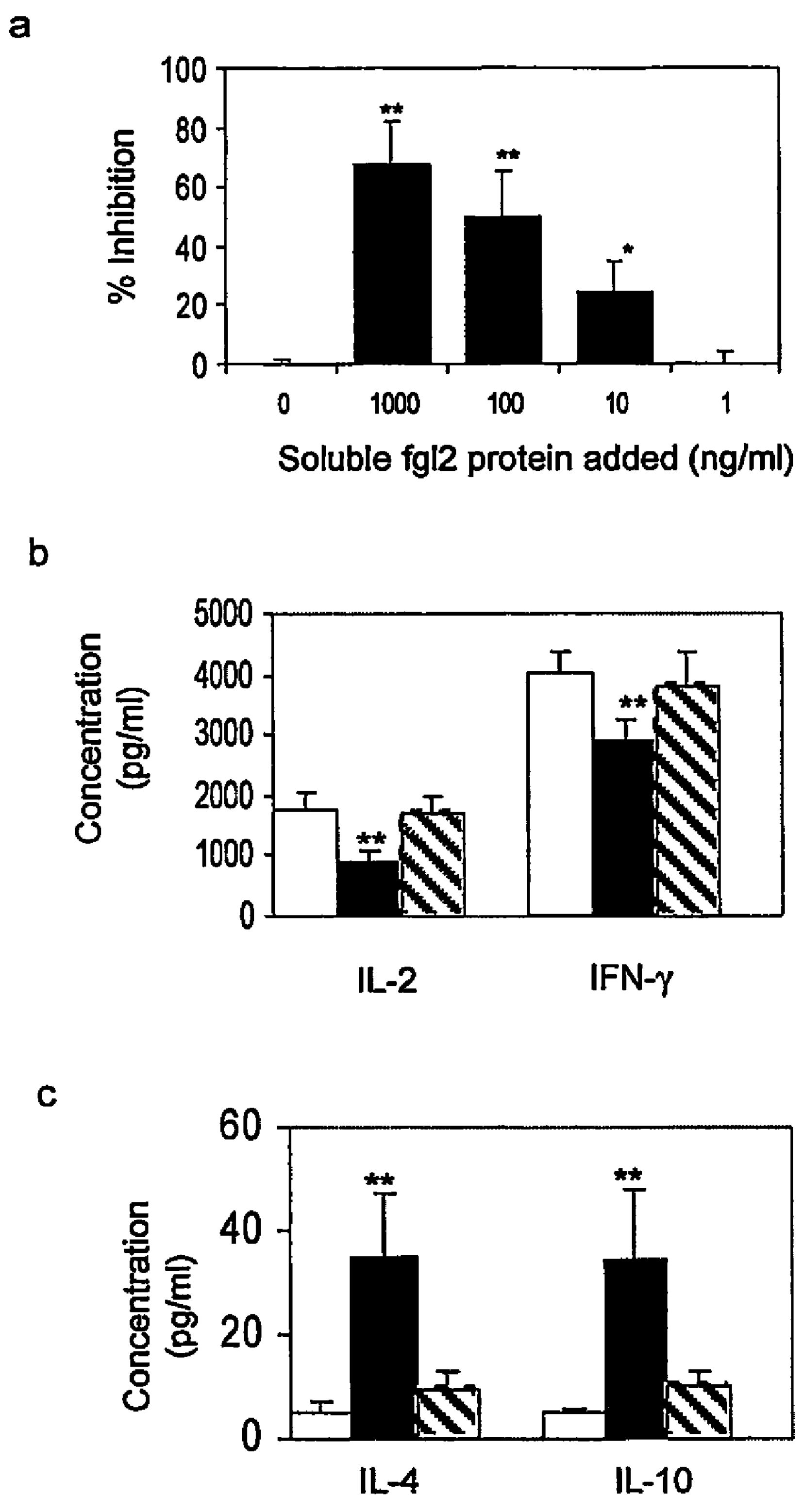
FIG. 5A-C shows soluble fgl2 protein (1 μg/ml) inhibited MLR with promotion of a Th2 cytokine profile. (a) Lymph node T cells were co-cultured with allogeneic BM-derived DC as described in the "Materials and Methods". soluble fgl2 protein (1 ng/ml to 1 μg/ml) was added to the culture at the beginning (d 0) and cell proliferation was measured using [$^3$H] thymidine as described. The incorporation of [$^3$H] thymidine in soluble fgl2-untreated control cultures (shown as 0 ng/ml soluble fgl2 protein added) was: 5,546±620 cpm with background 355±55 cpm. The data are expressed as percentage inhibition (fgl2-untreated cultures shown as 0% inhibition). (b & c) Supernatants from the allogeneic cultures in the absence (open bar) or presence of 1 μg/ml soluble fgl2 protein (closed bar) or 1 ng/ml soluble fgl2 protein (hatched bar) were collected at 24 h to measure the levels of cytokine produced. The data are representative of three separate experiments. **, p<0.01 and *, p<0.05 compared with control groups (far left, no soluble fgl2 was added).

To characterize further the effect of soluble fgl2 on allogeneic responses, the inventor cultured T cells with irradiated allogeneic BM-derived LPS-induced mature DC in the presence of soluble fgl2 protein. A similar dose-specific soluble fgl2 suppressive effect on alloreactive T cell proliferation was observed to that seen in FIG. 3. FIG. 5*a* shows that 1 μg/ml of soluble fgl2 protein resulted in a maximal 68±14% inhibition of T cell proliferation. Supernatants collected from these cultures (1 μg/ml of soluble fgl2) showed decreased levels of IL-2 and IFN-γ, no effect on levels of IL-12 and increased levels of IL-4 and IL-10 productions in comparison to supernatants from soluble fgl2-untreated allogeneic cultures (FIGS. 5B & C). The possibility that this alteration in cytokine response was due to direct toxicity was further examined. Soluble fgl2 did not cause non specific changes in cell survival of stimulated or unstimulated cells as discussed further below. In addition, the inventor did not observe any inhibition of CTL induction in the presence of soluble fgl2. Thus percent lysis at 5 days in control cultures (no fgl2) at 50:1 effector: target was (30±5%), whereas in fgl2-treated cultures lysis was 31±3% (p=0.74). The addition of soluble fgl2 protein to the allogeneic cultures at a concentration of 1 ng/ml had no inhibitory effect on T cell proliferation, and resulted in a promotion of Th1 cytokines expression, similar to that observed in soluble fgl2 untreated cultures (FIGS. 5B & C).

Soluble fgl2 did not Suppress T Cell Proliferation Via Induction of Apoptosis

Others have reported that certain immunosuppressive agents suppress T cell proliferation by inducing T cell apoptosis (23). Therefore, T cell viability was examined by both trypan blue dye exclusion and PI staining of lymphocyte nuclei after a 12 h-exposure to soluble fgl2 protein. At all concentrations of soluble fgl2 tested in this study, no significant differences in cell number and amount of apoptotic cells were detected between the soluble fgl2-treated T cells and untreated T cells (data not shown), suggesting that the inhibitory effects of soluble fgl2 were not an outcome of a nonspecific or cytotoxic effect.

Figure 6:
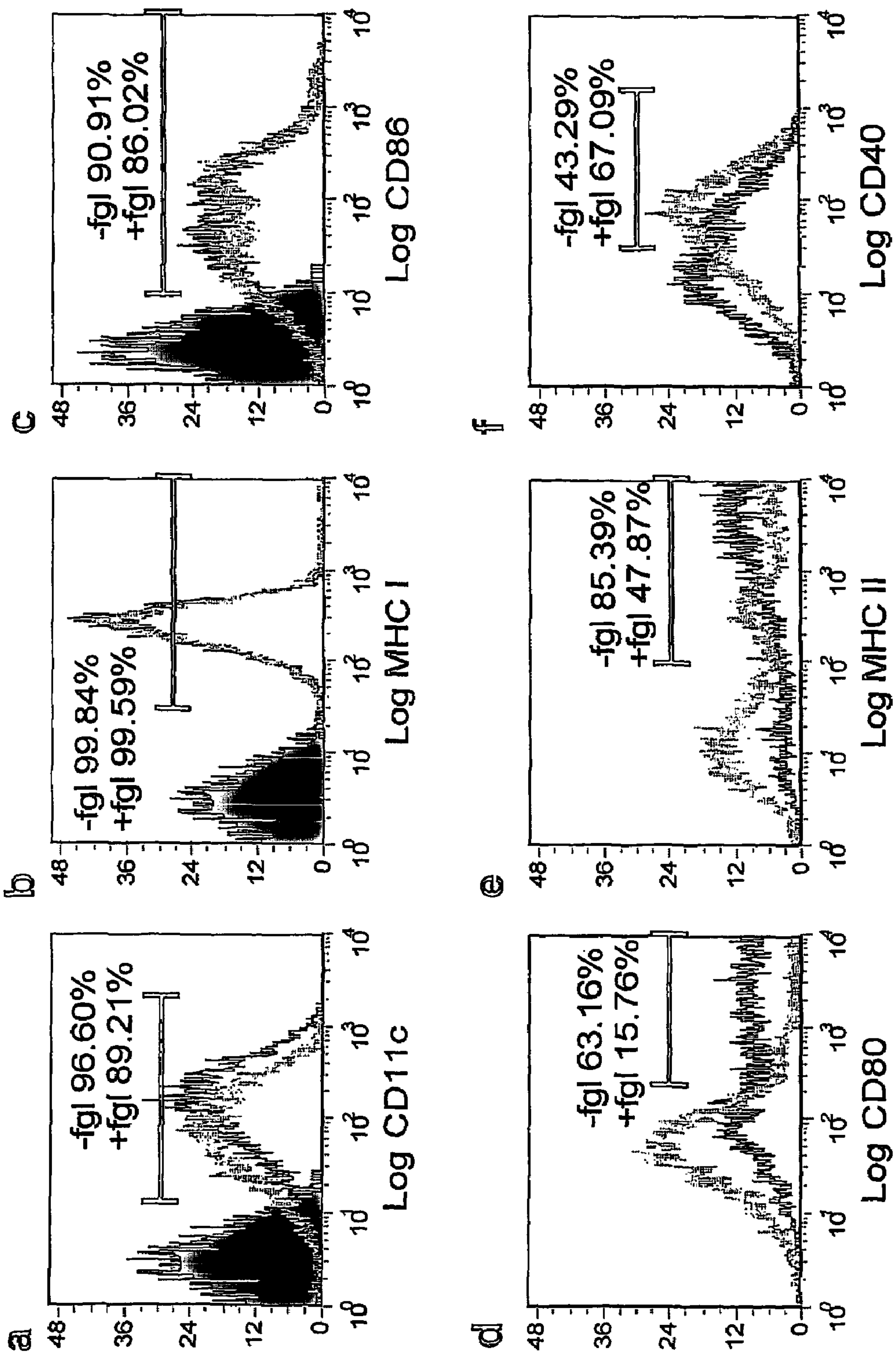
FIG. 6A-F shows cell surface phenotype of DC generated in the absence (control) or presence of soluble fgl2 (1 μg/ml) during maturation. BM cells were prepared and cultured for 7 d in the presence of GM-CSF and IL-4 to derive immature DC as described in the "Materials and Methods". Immature DCs were stimulated with LPS (200 ng/ml) to reach final maturation for 2 days in the absence and presence of soluble fgl2 protein. The expression of surface molecules including CD11c, CD80, CD86, MHC class I and class II and CD40 were measured by flow cytometry analysis. Results are representative of 3 independent experiments. Gray lines show fluorescence signals of cells treated with soluble fgl2, and stained with the specific Abs. Black lines represent non-soluble fgl2-treated cells. The blue shaded areas are the appropriate isotype-matched Ig control.

Soluble fgl2 Led to Reduced Expression of $CD80^{hi}$ and MHC Class $II^{hi}$ Molecules by BM-Derived DC The inventor next examined whether soluble fgl2 had the ability to impair the maturation of BM-derived DC. To test this, immature DC were generated by culturing BM cells with GM-CSF and IL-4 for 7 d. Following the addition of LPS, in the presence or absence of soluble fgl2 (1 μg/ml), the phenotype of these DC were examined by staining of cells with various mAbs followed by flow cytometry analysis. As shown in FIG. 6*a*, $CD11c^+$ cells composed the majority of both soluble fgl2-treated and non-treated cells, suggesting that the addition of soluble fgl2 did not reduce the number or viability of LPS-treated DC. Furthermore, the expression of MHC class I and CD86 was not altered by soluble fgl2 (FIGS. 6*b* and 6*c*). A minor change in CD40 expression was observed (FIG. 6*f*). However, incubation of DC with soluble fgl2 during LPS-induced maturation significantly reduced expression of both, $CD80^{hi}$ (FIG. 6*d*) MHC class $II^{hi}$ (FIG. 6*e*) and $CD80^{hi}$ (FIG. 6*d*) expression on DC. These findings suggest that soluble fgl2 inhibits LPS-induced DC maturation.

Figure 7:
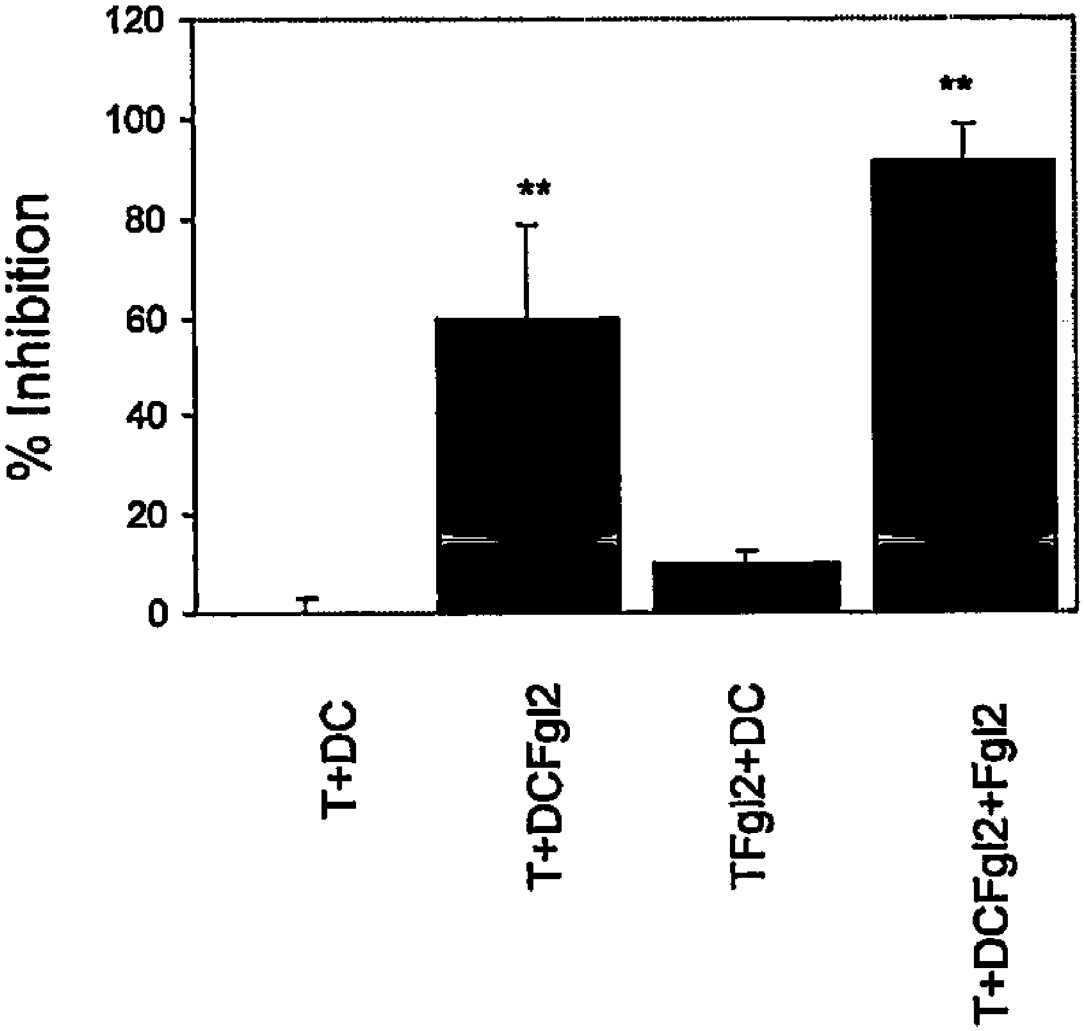
FIG. 7 shows DC treated with soluble fgl2 during LPS-induced maturation exhibited impaired ability to induce allogeneic responses. DC treated with soluble fgl2 (1 μg/ml) during LPS-induced maturation (DCFgl2) and T cells treated with soluble fgl2 protein (1 μg/ml) prior culturing with DC (TFgl2) were used to examine their ability to induce allogeneic response as described in the "Materials and Methods". In some cases, DC treated with soluble fgl2 during maturation (DCFgl2) were employed to activate allogeneic T cell proliferation with soluble fgl2 protein (1 μg/ml) added to the culture (last column). Proliferation was determined by [$^3$H] thymidine uptake in triplicate wells and the uptake in untreated cultures (shown as T+DC) was: 5,546±620 cpm with background 355±55 cpm. The data are representative of three separate experiments. **, p<0.01 and *, p<0.05 compared with control groups (second left, no soluble fgl2 was added).

Addition of Soluble Fgl2 During DC Maturation Abolished their Ability to Induce Allogeneic Responses To further examine the effect of soluble fgl2 protein on DC maturation, the inventor determined the ability of soluble fgl2-treated DC to stimulate allogeneic responses. FIG. 7 shows that DC treated with soluble fgl2 (1 μg/ml) during the LPS-induced maturation had an impaired ability to stimulate naive allogeneic T cell proliferation, in comparison to soluble fgl2-untreated DC. When naive T cells were pretreated with soluble fgl2 protein (1 μg/ml) for 12 h, washed, then cultured with allogeneic LPS-induced mature DC, no inhibitory effect on T cell proliferation was observed. This was compared to the levels of proliferation observed in cultures containing untreated control T cells stimulated with allogeneic LPS-induced mature DC. Maximal abrogation on alloreactive T cell proliferation was resulted when naïve T cells were stimulated with soluble fgl2-preexposed DC in the presence of soluble fgl2 protein (1 μg/ml).

Figure 8A:
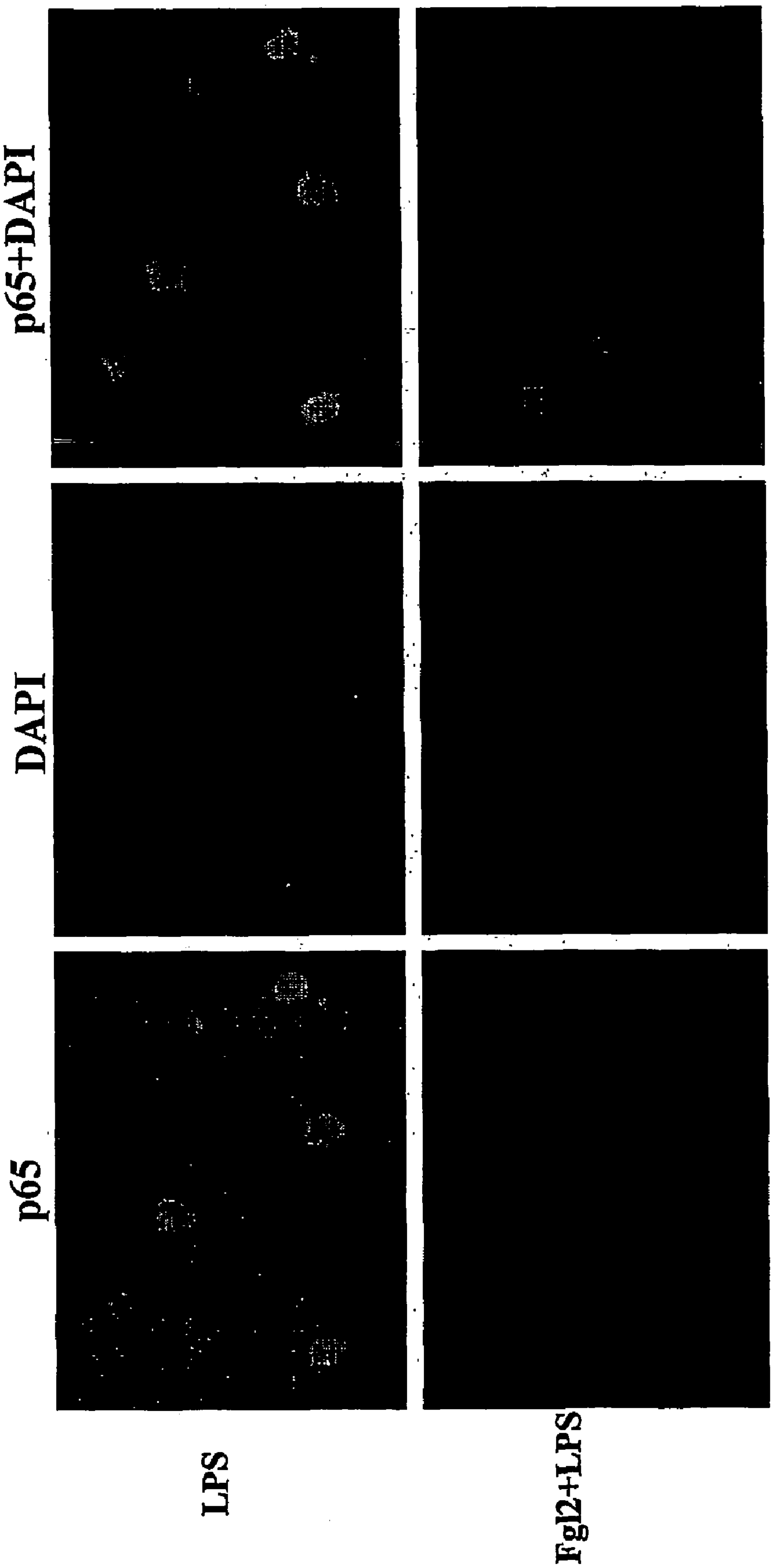
FIGS. 8A and B shows the effect of soluble fgl2 on translocation of NF-κB in LPS Stimulated Dendritic Cells. A, Dual immunofluorescence staining of LPS and soluble fgl2+
Figure 8B:
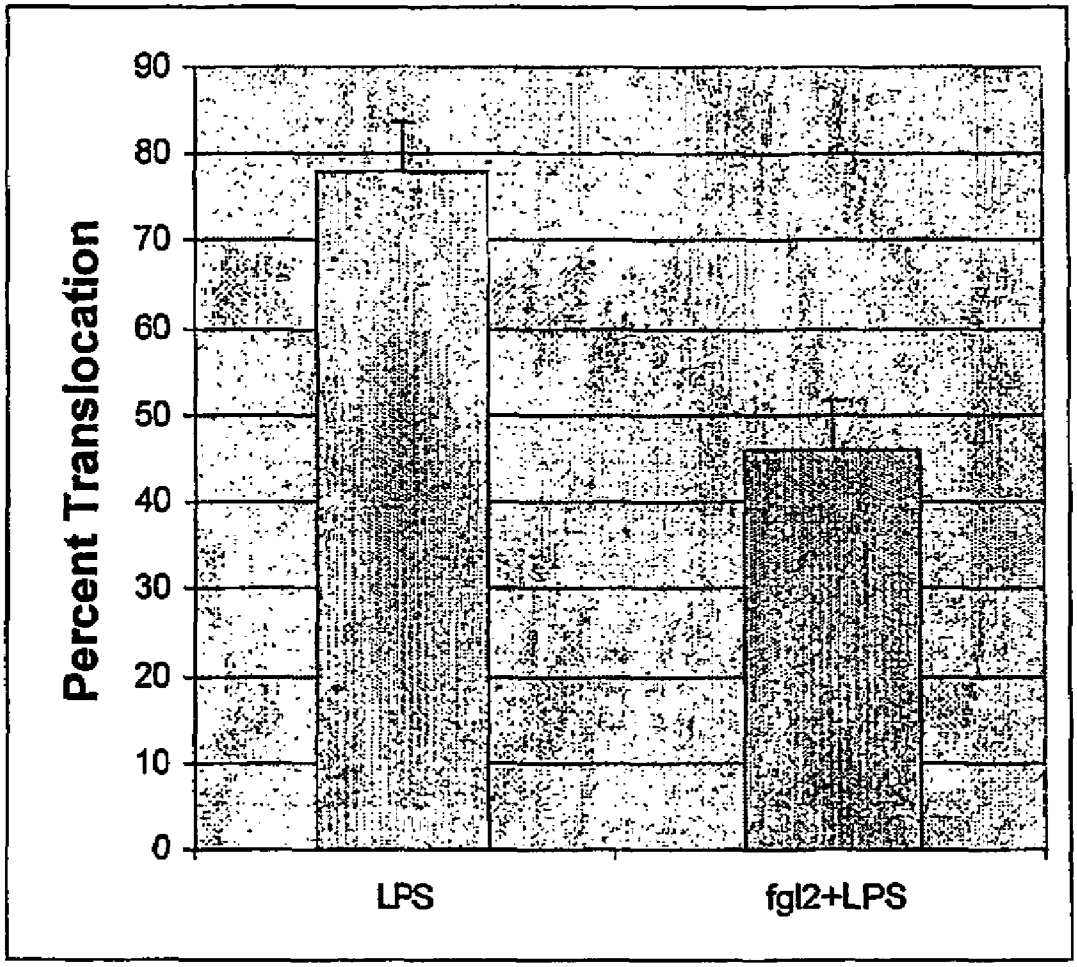

To examine whether soluble fgl2 prevents the maturation of BM-derived DC through the NF-κB pathway, BM-derived DC were stimulated with LPS (1 μg/ml) following 7 days of incubation in GM-CSF and recombinant mouse IL-4 in the presence or absence of soluble fgl2 protein (1 μg/ml) which was added at the same time of LPS exposure. The dendritic cells were examined at 5, 15, 30, 60, 120, and 240 min for NF-κB translocation by IF microscopy. To clearly determine if there was nuclear translocation, dual staining with a primary antibody to the p65 subunit of NF-κB and DAPI nuclear staining was used. Translocation of NF-κB occurred at all times examined, but was maximal after 1 h of LPS stimulation. NF-κB trans location was significantly reduced by the presence of soluble fgl2 protein at all time points examined (FIG. 8).

Discussion

The inventor has had a long interest in defining the regulation of induction and mechanism(s) of action of fgl2/fibroleukin, a novel protein that is expressed by both reticuloendothelial cells (macrophages and endothelial cells) and T cells. Fgl2 is a 432-amino acid protein that shares homology to the β and γ chains of fibrinogen with a FRED at the carboxyl-terminus (amino acids 202-432). When fgl2 is expressed as a membrane-associated protein in activated macrophages and endothelial cells, it exhibits a coagulation activity capable of directly cleaving prothrombin to thrombin. The membrane associated-fgl2 prothrombinase with the ability to directly generate thrombin plays an important role in innate immunity.

A protein belonging to the fibrinogen-like superfamily has been shown to exhibit immunomodulatory property. Tenascin, which shares a 40% homology to the FRED region of fgl2, blocks T cell activation induced by a soluble antigen, alloantigens, or ConA. The mechanism by which tenascin blocks T cell activation remains undefined. Recently, a soluble form of fgl2/fibroleukin (soluble fgl2) has been described, and of particular interest to the current study is the discovery that T cells are known to express soluble fgl2. Nevertheless, the function(s) of soluble fgl2 remains unexplored.

The inventor examined the role of soluble fgl2 in regulating the function of APC, in particular, DC. BM-derived DC were prepared and the effect of soluble fgl2 on LPS-induced maturation was examined. The inventor found that soluble fgl2 prevented the maturation of BM-derived DC by inhibiting the expression of CD80$^{hi}$, and MHC class II$^{hi}$ molecules, while having no significant effects on MHC class 1, CD11c and CD86 expression. These data are consistent with the observation that soluble fgl2-treated DC had a markedly reduced capacity to stimulate T cell proliferation in an allogeneic MLR and inhibit a Th1 cytokine response. Interestingly, further abrogation on alloreactive T cell proliferation was achieved when naïve T cells were stimulated with soluble fgl2-preexposed DC in the presence of soluble fgl2 protein (1 μg/ml), suggesting that soluble fgl2 exerts an immunosuppressive effect on T cells in addition to its effect on DC maturation.

The inventor has, in addition, explored evidence for a more direct effect of soluble fgl2 on T cells by examining the effect of soluble fgl2 on T cells by exploring its effect on T cell proliferation stimulated under different stimuli. In this study, the inventor showed that soluble fgl2 inhibited T cell proliferation induced by alloantigen, anti-CD3/CD28 or Con A. Although fgl2 shares a 36% homology to the β and γ chains of fibrinogen within the FRED, fibrinogen did not exhibit an immunosuppressive effect on T cell proliferation. This suggests the specificity of the immunosuppressive effect of soluble fgl2 on T cell proliferation.

The hypothesis that soluble fgl2 has a direct influence on T cells is supported by the inventor's findings that soluble fgl2 suppresses T cell proliferation induced by anti-CD3/CD28 mAbs and Con A. Soluble fgl2 may also act directly on APC to inhibit T cell proliferation in MLC.

The immunosuppressive effects of soluble fgl2 on alloreactive T cell proliferation was neutralized by a mAb having no inhibitory effect on the coagulation activity of fgl2, a function which is known to reside in "domain 1" of the molecule, a region distinct from "domain 2" which is the FRED-containing C terminal region. Similarly, a polyclonal Ab which possesses the ability to neutralize the fgl2 prothrombinase activity and which interacts with "domain 1" of the fgl2 molecule had no inhibitory effect on the immunosuppressive activity of soluble fgl2. Taken together, the inventor postulates that distinct domains of fgl2 are responsible for the prothrombinase and immunomodulatory activities of the molecule.

DC themselves are professional APCs which exhibit an ability to stimulate both naïve and memory T lymphocytes following their maturation (24, 25). The DC maturation process involves increased expression of surface MHC class II and costimulatory molecules and occurs in vivo as DC pass from the periphery to T cell areas of secondary lymphoid tissue. BM-derived DC deficient in costimulatory molecules can induce T cells to undergo a state of hyporesponsiveness, leading to prolongation of islet and cardiac allograft survival (25, 26) and inhibition of autoimmune disease progression in a variety of animal models (27).

The mechanism(s) by which soluble fgl2 alters the expression of CD80 and MHC class II was examined in the present studies. Nuclear translocation of members of the NF-κB family, particularly RelB, have been shown to be required for myeloid DC maturation (27, 31, 32). By immunflourescence microscopy, it was shown that soluble fgl2 markedly inhibits NF-κB translocation which may account for lack of maturation of DC as indicated by lack of expression of CD80$^{hi}$ and MHC Class II. The fact that not all DC were inhibited by soluble fgl2 may reflect dosage requirements as well as the fact that the population of DC are not homogeneous.

In the present studies, soluble fgl2 was shown to promote a Th2-cytokine profile (IL-4 and IL-10) during the initiation of the allogeneic response. Cytokines produced by Th2 cells have been shown to exhibit anti-inflammatory activities by regulating the development and activity of Th1 cells, which are in general associated with the development of autoimmunity, delayed-type hypersensitivity (DTH) and cell-mediated immune responses (33-35). Both IL-4 and IL-10 have been shown to antagonize development of Th1 cells, likely through decreasing expression/function of the cytokine IL-12, while promoting the differentiation of Th2 cells. In human and animal studies, polarization towards type-2 cytokine production has been associated with improved survival of allogeneic transplants (21, 35). Whether soluble fgl2 would affect graft survival in transplantation remains to be examined. Note in this report that soluble fgl2 had no effect on CTL activity in an allo mixed lymphocyte culture (MLC).

The actual mechanism(s) by which soluble fgl2 promotes a Th2 cytokine differentiation is not known. However, it is known that the differentiation of naïve CD4+ T cells into different populations of cytokine-secreting effector cells is influenced not only by the cytokine milieu in which differentiation takes place, but by a variety of accessory molecule interactions. The interaction of CD28 with CD86 (36, 37), CD4 with MHC class II (38, 39) and Ox-40 with Ox-40 ligand (40) have all been suggested to promote Th2 differentiation at the expense of Th1 differentiation, whereas CD28 interaction with CD80 on antigen presenting cells such as DC have been proposed to produce a Th1 response. Thus, preservation of CD86 and loss of CD80 and MHC Class II may explain the preferential bias towards Th2 cytokine production observed.

In summary, the inventor has reported that while membrane-bound fgl2 acts as a prothrombinase, soluble fgl2 is an immunomodulatory protein which has the ability to modulate T cell responses, and perhaps more importantly, alter DC maturation to favor production of tolerogenic DC. Currently, the use of non-specific immunosuppressive drugs to treat transplant rejection and autoimmune diseases is fraught with complications caused by drug toxicity and other adverse (immunologically) non-specific side effects. The inhibition of CD80 interaction with CD28 has been shown to have significant immunosuppressive effects including (but not limited to) the reduction of specific Ab production; prolongation of the survival of organ transplants; and the inhibition of autoimmune diabetes and lupus. Thus the direct immunosuppressive activity of soluble fgl2 on T cells and its ability to prevent the expression of costimulatory molecules on LPS-stimulated DC would allow potential strategy in treating autoimmune disorders and transplant rejection.

Here the inventor shows that soluble fgl2 has a potent immunomodulatory function. The findings that soluble fgl2 inhibited T-cell proliferation, promoted Th2 cytokines expression and prevented DC maturation suggest a novel usage of soluble fgl2 protein as an immunosuppressive agent which may impair DC maturation. This has broad implications in the treatment of allograft rejection and other immune-regulated diseases.

Example 2

Immunomodulatory Effects of Soluble Fgl2

Fibrinogen-related proteins have been shown to have immuoregulatory activities. It is believed that fgl2 also exerts immunoregulatory functions due to the presence of a FRED region near its C-terminal. To test this, the immunoregulatory property of fgl2 was tested in a one-way xenogeneic mixed lymphocyte reaction (see Methods). A rat (Wistar) to mouse (Balb/c) skingraft transplant was performed and the mice were primed with the skingraft for 13 days. Responder T cells were harvested from the lymph nodes of the skingraft recipient and stimulated with mitomycin C inactivated splenic cells of the Wistar rat origin in vitro in the presence of purified fgl2 protein. FIG. 9 shows that fgl2 protein inhibited xenogeneic T cell proliferation in a dose-dependent manner. At the highest concentration of fgl2 protein (1 μg/ml) used in the experiment, 30±8.4% inhibition of T cell proliferation was observed.

Example 3

Identification of Putative Fgl2 Molecular Variants

It has been shown that fgl2 is a secreted protein in T cells but is also believed that fgl2 is a type II transmembrane protein in macrophages due to the presence of a hydrophobic region near the N-terminal and the requirement of phospholipids to function as a prothrombinase. In order to determine whether structural protein variants existed to account for both a secreted and a transmembrane form of fgl2 protein, various cell types of the immune system were examined for putative fgl2 mRNA molecular variants that could generate structurally distinct proteins. 5' Rapid Amplification of cDNA Ends (5'RACE) analysis of murine fgl2 gene expression was performed on mRNAs isolated from naïve T cells, Con A-stimulated T cells (5 μg/ml Con A stimulation for 3 days), naïve B cells, LPS-stimulated B cells (10 μg/ml LPS for 3 days), immature and mature dendritic cells, naïve macrophages, and IFN-γ-stimulated macrophages (100 U/ml IFN-γ for 24 hrs). FIG. 10 shows full length 1.3 kb mRNA fgl2 transcripts were expressed in naïve T cells as well as the antigen presenting cells: LPS-stimulated B cells, immature and mature dendritic cells, naïve macrophages, and IFN-γ-stimulated macrophages. In contrast, no fgl2 mRNA transcript was present in naïve B cells and Con A-stimulated T cells expressed three shorter mRNA fgl2 transcripts corresponding to molecular sizes, 1.2 kb, 1.0 kb and 0.8 kb.

Example 4

Characterization of Fgl2 Molecular Variants in Concanavalin A-Stimulated T Cells The three shorter fgl2 mRNA transcripts seen in Con A-stimulated T cells can be the result of alternative splicing at the exon-intron junction, or alternative transcriptional start sites at the 5' end of the gene. In order to characterize these fgl2 mRNA variants, the 5'RACE products were purified from the agarose gel, subcloned into the vector, TOPO pCR2.1 and the inserts of the resulting plasmids were subsequently sequenced using primers specific for TOPO pCR2.1. The sequences of the 1.3 kb band observed in the antigen presenting cells and naïve T cells (FIG. 10) corresponded to the full length fgl2 mRNA that was previously described as necessary to express the fgl2 protein with the prothrombinase activity (FIG. 11) (42). The sequences of the three shorter fgl2 mRNA transcripts (1.2 kb, 1.0 kb and 0.8 kb shown in FIGS. 12-15) revealed the partial deletions of the transcripts were not due to alternative splicing at the exon-intron junction but rather the result of 5' end truncation of the mRNAs indicating they were the products of alternative transcriptional start sites (FIG. 11). The longest open reading frames of the 1.2 kb, 1.0 kb and 0.8 kb fragments as determined by the first methionine codon with a Kozak consensus sequence would begin translation at the ATG nucleotide position +217, +475, and +577, respectively (with the reference position of the first methionine ATG codon leading to the translation of the full length fgl2 protein as +1, FIG. 11). These open reading frames are also in frame with the one that generates a full length fgl2 protein with the prothrombinase activity. All three of the predicted amino acid sequence of the truncated fgl2 proteins lack the hydrophobic region and the signal peptide sequence present in the full length fgl2 protein.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Doolittle, R. F. 1983. The structure and evolution of vertebrate fibrinogen. *Ann N Y Acad Sci* 408:13.
2. Procopio, W. N., P. I. Pelavin, W. M. Lee, and N. M. Yeilding. 1999. Angiopoietin-1 and -2 coiled coil domains mediate distinct homo-oligomerization patterns, but fibrinogen-like domains mediate ligand activity. *J Biol Chem* 274:30196.
3. Chiquet-Ehrismann, R., C. Hagios, and K. Matsumoto. 1994. The tenascin gene family. *Perspect Dev Neurobiol* 2:3.
4. Tsakadze, N. L., Z. Zhao, and S. E. D'Souza. 2002. Interactions of intercellular adhesion molecule-1 with fibrinogen. *Trends Cardiovasc. Med* 12:101.
5. Sitrin, R. G., P. M. Pan, S. Srikanth, and R. F. Todd, 3rd. 1998. Fibrinogen activates NF-kappa B transcription factors in mononuclear phagocytes. *J Immunol* 161:1462.
6. Papapetropoulos, A., G. Garcia-Cardena, T. J. Dengler, P. C. Maisonpierre, G. D. Yancopoulos, and W. C. Sessa. 1999. Direct actions of angiopoietin-1 on human endothelium: evidence for network stabilization, cell survival, and interaction with other angiogenic growth factors. *Lab Invest* 79:213.
7. Hemesath, T. J., L. S. Marton, and K. Stefansson. 1994. Inhibition of T cell activation by the extracellular matrix protein tenascin. *J Immunol* 152:5199.
8. Ruegg, C. R., R. Chiquet-Ehrismann, and S. S. Alkan. 1989. Tenascin, an extracellular matrix protein, exerts immunomodulatory activities. *Proc Natl Acad Sci USA* 86:7437.
9. Ding, J. W., Q. Ning, M. F. Liu, A. Lai, J. Leibowitz, K. M. Peltekian, E. H. Cole, L. S. Fung, C. Holloway, P. A. Marsden, H. Yeger, M. J. Phillips, and G. A. Levy. 1997. Fulminant hepatic failure in murine hepatitis virus strain 3 infection: tissue-specific expression of a novel fgl2 prothrombinase. *J Virol* 71:9223.
10. Clark, D. A., G. Chaouat, P. C. Arck, H. W. Mittruecker, and G. A. Levy. 1998. Cytokine-dependent abortion in CBA×DBA/2 mice is mediated by the procoagulant fgl2 prothrombinase [correction of prothombinase]. *J Immunol* 160:545.
11. Clark, D. A., J. W. Ding, G. Yu, G. A. Levy, and R. M. Gorczynski. 2001. Fgl2 prothrombinase expression in mouse trophoblast and decidua triggers abortion but may be countered by OX-2. *Mol Hum Reprod* 7:185.
12. Koyama, T., L. R. Hall, W. G. Haser, S. Tonegawa, and H. Saito. 1987. Structure of a cytotoxic T-lymphocyte-specific gene shows a strong homology to fibrinogen beta and gamma chains. *Proc Natl Acad Sci USA* 84:1609.
13. Levy, G., and M. Abecassis. 1989. Activation of the immune coagulation system by murine hepatitis virus strain 3. *Rev Infect Dis* 11 *Suppl* 4:S712.
14. Parr, R. L., L. Fling, J. Reneker, N. Myers-Mason, J. L. Leibowitz, and G. Levy. 1995. Association of mouse fibrinogen-like protein with murine hepatitis virus-induced prothrombinase activity. *J Virol* 69:5033.
15. Fung, L. S., G. Neil, J. Leibowitz, E. H. Cole, S. Chung, A. Crow, and G. A. Levy. 1991. Monoclonal antibody analysis of a unique macrophage procoagulant activity induced by murine hepatitis virus strain 3 infection. *J Biol Chem* 266:1789.
16. Ding, J. W., Q. Ning, M. F. Liu, A. Lai, K. Peltekian, L. Fung, C. Holloway, H; Yeger, M. J. Phillips, and G. A. Levy. 1998. Expression of the fgl2 and its protein product (prothrombinase) in tissues during murine hepatitis virus strain-3 (MHV-3) infection. *Adv Exp Med Biol* 440:609.
17. Marazzi, S., S. Blum, R. Hartmann, D. Gundersen, M. Schreyer, S. Argraves, V. von Fliedner, R. Pytela, and C. Ruegg. 1998. Characterization of human fibroleukin, a fibrinogen-like protein secreted by T lymphocytes. *J Immunol* 161:138.
18. Ruegg, C., and R. Pytela. 1995. Sequence of a human transcript expressed in T-lymphocytes and encoding a fibrinogen-like protein. *Gene* 160:257.
19. Kohno, T., R. Moriuchi, S Katamine, Y. Yamada, M. Tomonaga, and T. Matsuyama. 2000. Identification of genes associated with the progression of adult T cell leukemia (ATL). *Jpn J Cancer Res* 91:1103.
20. Chan, C. W., M. W. Chan, M. Liu, L. Fung, E. H. Cole, J. L. Leibowitz, P. A. Marsden, D. A. Clark, and G. A. Levy. 2002. Kinetic analysis of a unique direct prothrombinase, fgl2, and identification of a serine residue critical for the prothrombinase activity. *J Immunol* 168:5170.
21. Gorczynski, R. M. 2001. Role of cytokines in allograft rejection. *Curr Pharm Des* 7:1039.
22. Brand, K., S. Page, G. Rogler, A. Bartsch, R. Brandl, R. Knuechel, M. Page, C. Kaltschmidt, P. A. Baeuerle, and D. Neumeier. 1996. Activated transcription factor nuclear factor-kappa B is present in the atherosclerotic lesion. *J Clin Invest* 97:1715.
23. Li, X. C., A. D. Wells, T. B. Strom, and L. A. Turka. 2000. The role of T cell apoptosis in transplantation tolerance. *Curr Opin Immunol* 12:522.
24. Morelli, A. E., H. Hackstein, and A. W. Thomson. 2001. Potential of tolerogenic dendritic cells for transplantation. *Semin Immunol* 13:323.
25. Lu, L., D. McCaslin, T. E. Starzl, and A. W. Thomson. 1995. Bone marrow-derived dendritic cell progenitors (NLDC 145+, MHC class II+, B7-1dim, B7-2−) induce alloantigen-specific hyporesponsiveness in murine T lymphocytes. *Transplantation* 60:1539.
26. Fu, F., Y. Li, S. Qian, L. Lu, F. D. Chambers, T. E. Starzl, J. J. Fung, and A. W. Thomson. 1997. Costimulatory molecule-deficient dendritic cell progenitors induce T cell hyporesponsiveness in vitro and prolong the survival of vascularized cardiac allografts. *Transplant Proc* 29:1310.
27. Lu, L., and A. W. Thomson. 2002. Manipulation of dendritic cells for tolerance induction in transplantation and autoimmune disease. *Transplantation* 73:S19.
28. Levy, G. A., M. Liu, J. Ding, S. Yuwaraj, J. Leibowitz, P. A. Marsden, Q. Ning, A. Kovalinka, and M. J. Phillips. 2000. Molecular and functional analysis of the human prothrombinase gene (HFGL2) and its role in viral hepatitis. *Am J Pathol* 156:1217.
29. Auffermann-Gretzinger, S., E. B. Keeffe, and S. Levy. 2001. Impaired dendritic cell maturation in patients with chronic, but not resolved, hepatitis C virus infection. *Blood* 97:3171.

30. Kakumu, S., S. Ito, T. Ishikawa, Y. Mita, T. Tagaya, Y. Fukuzawa, and K. Yoshioka. 2000. Decreased function of peripheral blood dendritic cells in patients with hepatocellular carcinoma with hepatitis B and C virus infection. *J Gastroenterol Hepatol* 15:431.

31. Koski, G. K., L. A. Lyakh, P. A. Cohen, and N. R. Rice. 2001. CD14+ monocytes as dendritic cell precursors: diverse maturation-inducing pathways lead to common activation of NF-kappab/RelB. *Crit Rev Immunol* 21:179.

32. Neumann, M., H. Fries, C. Scheicher, P. Keikavoussi, A. Kolb-Maurer, E. Brocker, E. Serfling, and E. Kampgen. 2000. Differential expression of Rel/NF-kappaB and octamer factors is a hallmark of the generation and maturation of dendritic cells. *Blood* 95:277.

33. Romagnani, S. 2000. T-cell subsets (Th1 versus Th2). *Ann Allergy Asthma Immunol* 85:9.

34. Lucey, D. R., M. Clerici, and G. M. Shearer. 1996. Type 1 and type 2 cytokine dysregulation in human infectious, neoplastic, and inflammatory diseases. *Clin Microbiol Rev* 9:532.

35. Ganschow, R., D. C. Broering, D. Nolkemper, J. Albani, M. J. Kemper, X. Rogiers, and M. Burdelski. 2001. Th2 cytokine profile in infants predisposes to improved graft acceptance after liver transplantation. *Transplantation* 72:929.

36. Ranger, A. M., M. P. Das, V. K. Kuchroo, and L. H. Glimcher. 1996. B7-2 (CD86) is essential for the development of IL-4-producing T cells. *Int Immunol* 8:1549.

37. Rulifson, I. C., A. I. Sperling, P. E. Fields, F. W. Fitch, and J. A. Bluestone. 1997. CD28 costimulation promotes the production of Th2 cytokines. *J Immunol* 158:658.

38. Fowell, D. J., J. Magram, C. W. Turck, N. Killeen, and R. M. Locksley. 1997. Impaired Th2 subset development in the absence of CD4. *Immunity* 6:559.

39. Fowell, D. J., K. Shinkai, X. C. Liao, A. M. Beebe, R. L. Coffman, D. R. Littman, and R. M. Locksley. 1999. Impaired NFATc translocation and failure of Th2 development in Itk-deficient CD4+ T cells. *Immunity* 11:399.

40. Delespesse, G., Y. Ohshima, L. P. Yang, C. Demeure, and M. Sarfati. 1999. OX40-Mediated cosignal enhances the maturation of naive human CD4+ T cells into high IL-4-producing effectors. *Int Arch Allergy Immunol* 118:384.

41. Yuwaraj, S., Ding, J., Liu, M., Marsden, P. A. & Levy, G. A. Genomic Characterization, Localization, and Functional Expression of FGL2, the Human Gene Encoding Fibroleukin: A Novel Human Procoagulant. Genomics 71, 330-338 (2001).

42. Qureshi, S. T., S. Clermont, J. Leibowitz, L. S. Fung, G. Levy, and D. Malo. 1995. Mouse hepatitis virus-3 induced prothrombinase (Fgl2) maps to proximal chromosome 5. Genomics 29:307.

I claim:

1. A method of suppressing an immune response to a transplanted organ or tissue in an animal comprising administering an effective amount of a soluble fgl2/fibroleukin protein consisting of the amino acid sequence shown in SEQ ID NO:2, wherein the organ or tissue is an allograft.

2. A method according to claim 1 to inhibit dendritic cell maturation.

3. A method according to claim 1 to promote a Th2 cytokine response.

4. The method according to claim 1 wherein the transplanted organ or tissue is selected from the group consisting of heart, liver, kidney, lung, pancreas, pancreatic islets, brain tissue, cornea, bone, intestine, skin and haematopoietic cells.

5. The method according to claim 4 wherein the tissue or organ is skin.

6. The method according to claim 1 wherein the animal is a human.

* * * * *

SEQUENCE LISTING

```
<160> NUMBER OF SEQ ID NOS: 8

<210> SEQ ID NO 1
<211> LENGTH: 1083
<212> TYPE: DNA
<213> ORGANISM: Mus musculus

<400> SEQUENCE: 1

atggaggagg tgctcaaaga agtgcggacc ctcaaggaag cagtggacag tctgaagaaa      60

tcctgccagg actgtaagtt gcaggctgac gaccatcgag atcccggcgg gaatggaggg     120

aatggagcag agacagccga ggacagtaga gtccaggaac tggagagtca ggtgaacaag     180

ctgtcctcag agctgaagaa tgcaaaggac cagatccagg ggctgcaggg gcgcctggag     240

acgctccatc tggtaaatat gaacaacatt gagaactacg tggacaacaa agtggcaaat     300

ctaaccgttg tggtcaacag tttggatggc aagtgttcca agtgtcccag ccaagaacac     360

atgcagtcac agccggttca acatctaata tacaaagatt gttccgacca ctacgtgcta     420

ggaaggagaa gcagtggggc ctacagagtt accctgatc acagaaacag cagctttgag      480

gtctactgtg acatggagac catgggtgga ggctggacgg tgctgcaggc tcgccttgat     540

ggcagcacca acttcaccag agagtggaaa gactacaaag ccggctttgg aaaccttgaa     600

cgagaatttt ggttgggcaa cgataaaatt catcttctga ccaagagtaa ggaaatgatt     660

ttgagaatag atcttgaaga ctttaatggt ctcacacttt atgccttgta tgatcagttt     720

tatgtggcta atgaatttct caaataccga ttacacatcg gtaactacaa tggcacggga     780

ggggatgcct tgcgtttcag tcgacactac aaccatgacc tgaggttttt cacaacccca     840

gacagagaca acgatcggta cccctctggg aactgtgggc tctattacag ctcaggctgg     900

tggtttgatt catgtctctc tgccaactta aatggcaaat attaccacca gaaatacaaa     960

ggtgtccgta atgggatttt ctggggcacc tggcctggta taaaccaggc acagccaggt    1020
```

-continued

```
ggctacaagt cctccttcaa acaggccaag atgatgatta ggcccaagaa tttcaagcca   1080

taa                                                                 1083


<210> SEQ ID NO 2
<211> LENGTH: 360
<212> TYPE: PRT
<213> ORGANISM: Mus musculus

<400> SEQUENCE: 2

Met Glu Glu Val Leu Lys Glu Val Arg Thr Leu Lys Glu Ala Val Asp
1               5                   10                  15

Ser Leu Lys Lys Ser Cys Gln Asp Cys Lys Leu Gln Ala Asp Asp His
            20                  25                  30

Arg Asp Pro Gly Gly Asn Gly Gly Asn Gly Ala Glu Thr Ala Glu Asp
        35                  40                  45

Ser Arg Val Gln Glu Leu Glu Ser Gln Val Asn Lys Leu Ser Ser Glu
    50                  55                  60

Leu Lys Asn Ala Lys Asp Gln Ile Gln Gly Leu Gln Gly Arg Leu Glu
65                  70                  75                  80

Thr Leu His Leu Val Asn Met Asn Asn Ile Glu Asn Tyr Val Asp Asn
                85                  90                  95

Lys Val Ala Asn Leu Thr Val Val Val Asn Ser Leu Asp Gly Lys Cys
            100                 105                 110

Ser Lys Cys Pro Ser Gln Glu His Met Gln Ser Gln Pro Val Gln His
        115                 120                 125

Leu Ile Tyr Lys Asp Cys Ser Asp His Tyr Val Leu Gly Arg Arg Ser
    130                 135                 140

Ser Gly Ala Tyr Arg Val Thr Pro Asp His Arg Asn Ser Ser Phe Glu
145                 150                 155                 160

Val Tyr Cys Asp Met Glu Thr Met Gly Gly Gly Trp Thr Val Leu Gln
                165                 170                 175

Ala Arg Leu Asp Gly Ser Thr Asn Phe Thr Arg Glu Trp Lys Asp Tyr
            180                 185                 190

Lys Ala Gly Phe Gly Asn Leu Glu Arg Glu Phe Trp Leu Gly Asn Asp
        195                 200                 205

Lys Ile His Leu Leu Thr Lys Ser Lys Glu Met Ile Leu Arg Ile Asp
    210                 215                 220

Leu Glu Asp Phe Asn Gly Leu Thr Leu Tyr Ala Leu Tyr Asp Gln Phe
225                 230                 235                 240

Tyr Val Ala Asn Glu Phe Leu Lys Tyr Arg Leu His Ile Gly Asn Tyr
                245                 250                 255

Asn Gly Thr Gly Gly Asp Ala Leu Arg Phe Ser Arg His Tyr Asn His
            260                 265                 270

Asp Leu Arg Phe Phe Thr Thr Pro Asp Arg Asp Asn Asp Arg Tyr Pro
        275                 280                 285

Ser Gly Asn Cys Gly Leu Tyr Tyr Ser Ser Gly Trp Trp Phe Asp Ser
    290                 295                 300

Cys Leu Ser Ala Asn Leu Asn Gly Lys Tyr Tyr His Gln Lys Tyr Lys
305                 310                 315                 320

Gly Val Arg Asn Gly Ile Phe Trp Gly Thr Trp Pro Gly Ile Asn Gln
                325                 330                 335

Ala Gln Pro Gly Gly Tyr Lys Ser Ser Phe Lys Gln Ala Lys Met Met
            340                 345                 350
```

-continued

```
Ile Arg Pro Lys Asn Phe Lys Pro
        355                 360


<210> SEQ ID NO 3
<211> LENGTH: 825
<212> TYPE: DNA
<213> ORGANISM: Mus musculus

<400> SEQUENCE: 3

atgaacaaca ttgagaacta cgtggacaac aaagtggcaa atctaaccgt tgtggtcaac      60

agtttggatg gcaagtgttc caagtgtccc agccaagaac acatgcagtc acagccggtt     120

caacatctaa tatacaaaga ttgttccgac cactacgtgc taggaaggag aagcagtggg     180

gcctacagag ttacccctga tcacagaaac agcagctttg aggtctactg tgacatggag     240

accatgggtg gaggctggac ggtgctgcag gctcgccttg atggcagcac caacttcacc     300

agagagtgga aagactacaa agccggcttt ggaaaccttg aacgagaatt ttggttgggc     360

aacgataaaa ttcatcttct gaccaagagt aaggaaatga ttttgagaat agatcttgaa     420

gactttaatg gtctcacact ttatgccttg tatgatcagt tttatgtggc taatgaattt     480

ctcaaatacc gattacacat cggtaactac aatggcacgg gaggggatgc cttgcgtttc     540

agtcgacact acaaccatga cctgaggttt ttcacaaccc cagacagaga caacgatcgg     600

taccccctctg ggaactgtgg gctctattac agctcaggct ggtggtttga ttcatgtctc     660

tctgccaact taaatggcaa atattaccac cagaaataca aaggtgtccg taatgggatt     720

ttctggggca cctggcctgg tataaaccag gcacagccag gtggctacaa gtcctccttc     780

aaacaggcca agatgatgat taggcccaag aatttcaagc cataa                     825


<210> SEQ ID NO 4
<211> LENGTH: 274
<212> TYPE: PRT
<213> ORGANISM: Mus musculus

<400> SEQUENCE: 4

Met Asn Asn Ile Glu Asn Tyr Val Asp Asn Lys Val Ala Asn Leu Thr
1               5                   10                  15

Val Val Val Asn Ser Leu Asp Gly Lys Cys Ser Lys Cys Pro Ser Gln
            20                  25                  30

Glu His Met Gln Ser Gln Pro Val Gln His Leu Ile Tyr Lys Asp Cys
        35                  40                  45

Ser Asp His Tyr Val Leu Gly Arg Arg Ser Ser Gly Ala Tyr Arg Val
    50                  55                  60

Thr Pro Asp His Arg Asn Ser Ser Phe Glu Val Tyr Cys Asp Met Glu
65                  70                  75                  80

Thr Met Gly Gly Gly Trp Thr Val Leu Gln Ala Arg Leu Asp Gly Ser
                85                  90                  95

Thr Asn Phe Thr Arg Glu Trp Lys Asp Tyr Lys Ala Gly Phe Gly Asn
            100                 105                 110

Leu Glu Arg Glu Phe Trp Leu Gly Asn Asp Lys Ile His Leu Leu Thr
        115                 120                 125

Lys Ser Lys Glu Met Ile Leu Arg Ile Asp Leu Glu Asp Phe Asn Gly
    130                 135                 140

Leu Thr Leu Tyr Ala Leu Tyr Asp Gln Phe Tyr Val Ala Asn Glu Phe
145                 150                 155                 160

Leu Lys Tyr Arg Leu His Ile Gly Asn Tyr Asn Gly Thr Gly Gly Asp
                165                 170                 175
```

-continued

```
Ala Leu Arg Phe Ser Arg His Tyr Asn His Asp Leu Arg Phe Phe Thr
            180                 185                 190

Thr Pro Asp Arg Asp Asn Asp Arg Tyr Pro Ser Gly Asn Cys Gly Leu
        195                 200                 205

Tyr Tyr Ser Ser Gly Trp Trp Phe Asp Ser Cys Leu Ser Ala Asn Leu
    210                 215                 220

Asn Gly Lys Tyr Tyr His Gln Lys Tyr Lys Gly Val Arg Asn Gly Ile
225                 230                 235                 240

Phe Trp Gly Thr Trp Pro Gly Ile Asn Gln Ala Gln Pro Gly Gly Tyr
                245                 250                 255

Lys Ser Ser Phe Lys Gln Ala Lys Met Met Ile Arg Pro Lys Asn Phe
            260                 265                 270

Lys Pro


<210> SEQ ID NO 5
<211> LENGTH: 723
<212> TYPE: DNA
<213> ORGANISM: Mus musculus

<400> SEQUENCE: 5

atgcagtcac agccggttca acatctaata tacaaagatt gttccgacca ctacgtgcta      60

ggaaggagaa gcagtggggc ctacagagtt acccctgatc acagaaacag cagctttgag     120

gtctactgtg acatggagac catgggtgga ggctggacgg tgctgcaggc tcgccttgat     180

ggcagcacca acttcaccag agagtggaaa gactacaaag ccggctttgg aaaccttgaa     240

cgagaatttt ggttgggcaa cgataaaatt catcttctga ccaagagtaa ggaaatgatt     300

ttgagaatag atcttgaaga ctttaatggt ctcacacttt atgccttgta tgatcagttt     360

tatgtggcta atgaatttct caaataccga ttacacatcg gtaactacaa tggcacggga     420

ggggatgcct tgcgtttcag tcgacactac aaccatgacc tgaggttttt cacaacccca     480

gacagagaca acgatcggta cccctctggg aactgtgggc tctattacag ctcaggctgg     540

tggtttgatt catgtctctc tgccaactta aatggcaaat attaccacca gaaatacaaa     600

ggtgtccgta atgggatttt ctggggcacc tggcctggta taaaccaggc acagccaggt     660

ggctacaagt cctccttcaa acaggccaag atgatgatta ggcccaagaa tttcaagcca     720

taa                                                                   723


<210> SEQ ID NO 6
<211> LENGTH: 240
<212> TYPE: PRT
<213> ORGANISM: Mus musculus

<400> SEQUENCE: 6

Met Gln Ser Gln Pro Val Gln His Leu Ile Tyr Lys Asp Cys Ser Asp
1               5                   10                  15

His Tyr Val Leu Gly Arg Arg Ser Ser Gly Ala Tyr Arg Val Thr Pro
            20                  25                  30

Asp His Arg Asn Ser Ser Phe Glu Val Tyr Cys Asp Met Glu Thr Met
        35                  40                  45

Gly Gly Gly Trp Thr Val Leu Gln Ala Arg Leu Asp Gly Ser Thr Asn
    50                  55                  60

Phe Thr Arg Glu Trp Lys Asp Tyr Lys Ala Gly Phe Gly Asn Leu Glu
65                  70                  75                  80

Arg Glu Phe Trp Leu Gly Asn Asp Lys Ile His Leu Leu Thr Lys Ser
```

-continued

```
                85                  90                  95

Lys Glu Met Ile Leu Arg Ile Asp Leu Glu Asp Phe Asn Gly Leu Thr
            100                 105                 110

Leu Tyr Ala Leu Tyr Asp Gln Phe Tyr Val Ala Asn Glu Phe Leu Lys
        115                 120                 125

Tyr Arg Leu His Ile Gly Asn Tyr Asn Gly Thr Gly Gly Asp Ala Leu
    130                 135                 140

Arg Phe Ser Arg His Tyr Asn His Asp Leu Arg Phe Phe Thr Thr Pro
145                 150                 155                 160

Asp Arg Asp Asn Asp Arg Tyr Pro Ser Gly Asn Cys Gly Leu Tyr Tyr
                165                 170                 175

Ser Ser Gly Trp Trp Phe Asp Ser Cys Leu Ser Ala Asn Leu Asn Gly
            180                 185                 190

Lys Tyr Tyr His Gln Lys Tyr Lys Gly Val Arg Asn Gly Ile Phe Trp
        195                 200                 205

Gly Thr Trp Pro Gly Ile Asn Gln Ala Gln Pro Gly Gly Tyr Lys Ser
    210                 215                 220

Ser Phe Lys Gln Ala Lys Met Met Ile Arg Pro Lys Asn Phe Lys Pro
225                 230                 235                 240


<210> SEQ ID NO 7
<211> LENGTH: 30
<212> TYPE: DNA
<213> ORGANISM: Artificial Sequence
<220> FEATURE:
<223> OTHER INFORMATION: Forward primer

<400> SEQUENCE: 7

tgccgcactg gatccatgag gcttcctggt                                      30


<210> SEQ ID NO 8
<211> LENGTH: 22
<212> TYPE: DNA
<213> ORGANISM: Artificial Sequence
<220> FEATURE:
<223> OTHER INFORMATION: Reverse primer

<400> SEQUENCE: 8

ttatggcttg aaattcttgg gc                                              22
```